(12) United States Patent
Pedersen et al.

(10) Patent No.: US 12,171,851 B2
(45) Date of Patent: *Dec. 24, 2024

(54) ANTIMICROBIAL COMPOSITIONS CONTAINING CATIONIC ACTIVE INGREDIENTS

(71) Applicant: ECOLAB USA INC., Saint Paul, MN (US)

(72) Inventors: Daniel E. Pedersen, Saint Paul, MN (US); Carter M. Silvernail, Saint Paul, MN (US); Kerrie E. Walters, Saint Paul, MN (US); Hilina Emiru, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/158,889

(22) Filed: Jan. 24, 2023

(65) Prior Publication Data

US 2023/0157937 A1    May 25, 2023

Related U.S. Application Data

(63) Continuation of application No. 15/160,580, filed on May 20, 2016, now Pat. No. 11,590,065, which is a continuation of application No. 14/225,039, filed on Mar. 25, 2014, now abandoned.

(51) Int. Cl.

| | | |
|---|---|---|
| *A01N 33/12* | (2006.01) | |
| *A01N 25/16* | (2006.01) | |
| *A01N 25/30* | (2006.01) | |
| *A01N 47/44* | (2006.01) | |
| *A61K 8/34* | (2006.01) | |
| *A61K 8/41* | (2006.01) | |
| *A61K 8/43* | (2006.01) | |
| *A61K 8/60* | (2006.01) | |
| *A61K 8/81* | (2006.01) | |
| *A61Q 17/00* | (2006.01) | |
| *A61Q 19/00* | (2006.01) | |
| *A61Q 19/10* | (2006.01) | |

(52) U.S. Cl.
CPC ............ *A61K 8/43* (2013.01); *A01N 25/16* (2013.01); *A01N 25/30* (2013.01); *A01N 33/12* (2013.01); *A01N 47/44* (2013.01); *A61K 8/345* (2013.01); *A61K 8/41* (2013.01); *A61K 8/416* (2013.01); *A61K 8/602* (2013.01); *A61K 8/8158* (2013.01); *A61Q 17/005* (2013.01); *A61Q 19/00* (2013.01); *A61Q 19/10* (2013.01); *A61K 2800/30* (2013.01); *A61K 2800/54* (2013.01); *A61K 2800/74* (2013.01)

(58) Field of Classification Search
CPC ........ A01N 33/12; A01N 25/30; A01N 25/16; A61K 8/416; A61K 8/345; A61K 8/8158; A61K 8/602; A61K 8/41; A61Q 19/00; A61Q 19/10

See application file for complete search history.

(56) References Cited

U.S. PATENT DOCUMENTS

| | | |
|---|---|---|
| 4,764,365 A | 8/1988 | Boothe et al. |
| 5,188,756 A | 2/1993 | Baker |
| 5,225,095 A | 7/1993 | DiMaio et al. |
| 5,234,618 A | 8/1993 | Kamegai |
| 5,415,814 A | 5/1995 | Ofosu |
| 5,417,893 A | 5/1995 | Ofosu |
| 5,635,462 A | 6/1997 | Fendler et al. |
| 5,653,970 A | 8/1997 | Vermeer |
| 5,707,959 A | 1/1998 | Pancheri |
| 5,756,446 A | 5/1998 | Bator |
| 6,057,274 A | 5/2000 | Bator |
| 6,221,828 B1 | 4/2001 | Matsuo |
| 6,323,171 B1 | 11/2001 | Fonsny |
| 6,384,004 B2 | 5/2002 | McCandlish |
| 6,387,866 B1 | 5/2002 | Mondin |
| 6,395,691 B1 | 5/2002 | Tsaur |
| 6,432,907 B1 | 8/2002 | Skold |
| 6,764,989 B1 | 7/2004 | Huish |
| 6,946,786 B2 | 1/2005 | Patel |
| 6,906,018 B1 | 6/2005 | Patel |
| 6,906,023 B1 | 6/2005 | Patel |

(Continued)

FOREIGN PATENT DOCUMENTS

| | | |
|---|---|---|
| CN | 103118655 A | 5/2013 |
| EP | 1669061 B1 | 6/2006 |

(Continued)

OTHER PUBLICATIONS

Mackernium 007N, Rhodia, INCI Name: Polyquaternium-7, Product Information N002497, 1 page Sep. 30, 2010.
Ecolab USA Inc., in connection with PCT/US2015/018370 filed Mar. 3, 2015, "Search Report", 3 pages.
Supplementary European Search Report, EP 15 76 8833 Oct. 23, 2017 2017.
Ecolab USA Inc., PCT/US2015/018370, filed Mar. 3, 2015, "International Search Report", mailed Jun. 3, 2015, 3 pages.
Buffet-Batallion et al., International Journal of Antimicrobial Agents, 39, 381-389 2012.
U.S. Appl. No. 14/449,895, filed Aug. 1, 2014.
Claesson et al., "Sugar Surfactants, Encyclopedia of Surface and Colloid Science" pp. 4909-4925 Dec. 31, 2002.
Coots, Robert J. et al., "New, Natural-based Quaternary Conditioners for Personal Care Applications" Sup. Jan. 2009, p. 1-9.

(Continued)

*Primary Examiner* — Irina Neagu
(74) *Attorney, Agent, or Firm* — McKee, Voorhees & Sease, PLC

(57) ABSTRACT

The antimicrobial composition of the present invention comprises a cationic active ingredient, a foam boosting surfactant, a foam boosting copolymer, a foam stabilizer, and a chelating agent. The present antimicrobial compositions are free of the antimicrobial agent triclosan (i.e., 2,4,4'-trichloro-2'hydroxy-diphenylether), have rapid cidal activity, provide stable copious foam and exhibit enhanced tissue (e.g. skin) compatibility as defined by an in vitro whole toxicology assessment method.

7 Claims, 8 Drawing Sheets

(56) References Cited

U.S. PATENT DOCUMENTS

| | | |
|---|---|---|
| 7,074,747 B1 | 7/2006 | Lukenbach et al. |
| 7,163,914 B2 | 1/2007 | Gluck |
| 7,179,779 B1 | 2/2007 | Hauser |
| 7,250,392 B1 | 7/2007 | Leonard |
| 7,345,015 B1 | 3/2008 | Kong et al. |
| 7,501,387 B2 | 3/2009 | Aihara |
| 7,507,399 B1 | 3/2009 | O'Lenick, Jr. |
| 7,544,649 B2 | 6/2009 | Aihara |
| 7,547,672 B2 | 6/2009 | Zaki |
| 7,709,430 B2 | 5/2010 | Mizushima |
| 9,956,153 B2 * | 5/2018 | Emiru ............ A61K 9/122 |
| 10,517,806 B2 | 12/2019 | Emiru et al. |
| 11,590,065 B2 * | 2/2023 | Pedersen ............ A61P 31/12 |
| 2001/0044393 A1 | 11/2001 | Peterson, Jr. et al. |
| 2002/0155978 A1 | 10/2002 | Man et al. |
| 2002/0183233 A1 | 12/2002 | Shuman |
| 2003/0022941 A1 | 1/2003 | Taylor et al. |
| 2003/0074742 A1 | 4/2003 | Perry |
| 2004/0136940 A1 | 7/2004 | Lazarowitz |
| 2005/0000030 A1 | 1/2005 | Dupont |
| 2005/0176614 A1 | 8/2005 | Soldanski |
| 2005/0215461 A1 | 9/2005 | Gluck et al. |
| 2006/0142174 A1 | 6/2006 | Fukuda |
| 2006/0172912 A1 | 8/2006 | Burt |
| 2008/0209645 A1 | 9/2008 | Carrillo |
| 2009/0069436 A1 | 3/2009 | MacGregor |
| 2010/0081596 A1 | 4/2010 | Rong |
| 2011/0118164 A1 | 5/2011 | Kimura et al. |
| 2012/0070341 A1 | 3/2012 | Eder et al. |
| 2012/0071438 A1 | 3/2012 | Pedersen et al. |
| 2013/0035396 A1 | 2/2013 | Moen et al. |

FOREIGN PATENT DOCUMENTS

| | | |
|---|---|---|
| EP | 1669061 B9 | 3/2010 |
| EP | 2260830 A1 | 12/2010 |
| JP | 2002514163 A | 5/2002 |
| JP | 2004224703 A | 8/2004 |
| JP | 2005154360 A | 6/2005 |
| JP | 2009242274 A | 10/2009 |
| JP | 2014502954 A | 2/2014 |
| WO | 9606619 A1 | 3/1996 |
| WO | 9801110 A1 | 1/1998 |
| WO | 2001007547 A1 | 2/2001 |
| WO | 2007068938 A2 | 6/2007 |
| WO | 2007068938 A3 | 6/2007 |
| WO | 2009029046 A1 | 3/2009 |
| WO | 2012038914 A2 | 3/2012 |
| WO | 2013148247 A2 | 10/2013 |

OTHER PUBLICATIONS

CCI, "Poly Suga Quat Series Natural, Green Conditioning Surfactants", 4 pages Oct. 24, 2013.

Simoes, Manuel et al., "Action of a cationic surfactant on the activity and removal of bacterial biofilms formed under different flow regimes" Water Research 39 (2005) 478-486.

Viscardi, Guido et al., "Synthesis and Surface and Antimicrobial Properties of Novel Cationic Surfactants" J. Org. Chem. 2000, 65, 8197-8203.

EP 1669061 B1—Merz Pharma Gmbh & Co—English Translation Jun. 14, 2006.

Ecolab USA Inc et al., PCT/IB2011/054157 filed Sep. 22, 2011, "International Search Report", 5 pages, mailed Jun. 13, 2012.

* cited by examiner

ANTIMICROBIAL COMPOSITIONS CONTAINING CATIONIC ACTIVE INGREDIENTS

CROSS REFERENCE TO RELATED APPLICATION

This is a continuation application of U.S. Ser. No. 15/160,580, filed May 20, 2016, now U.S. Pat. No. 11,590,065, which is a continuation application of U.S. Ser. No. 14/225,039, filed Mar. 25, 2014, both of which are herein incorporated by reference in their entirety.

FIELD OF THE INVENTION

The present invention is directed to antimicrobial compositions, like personal care compositions, having improved antimicrobial efficacy and high foaming attributes. More particularly, the present invention relates to antimicrobial compositions exhibiting the antimicrobial effectiveness of cationic active ingredients, a foam boosting surfactant, a chelating agent, a novel foam boosting copolymer, with optional properties of a broad spectrum of antimicrobial efficacy, high foam and reduced irritation to mammalian tissue. The composition is essentially free of aromatic biocides such as triclosan, anionic surfactants and $C_1$ to $C_4$ alcohols.

BACKGROUND OF THE INVENTION

Antimicrobial personal care compositions are known in the art. Especially useful are antimicrobial cleansing compositions, which typically are used to cleanse the skin and to destroy bacteria and other microorganisms present on the skin, especially the hands, arms, and face of the user.

Antimicrobial compositions are used, for example, in the health care industry; long term care, hospitality and health/exercise facilities; food service industry, meat processing industry, and in the private sector by individual consumers. The widespread use of antimicrobial compositions indicates the importance consumers place on controlling bacteria and other microorganism populations on skin. It is important, however, that antimicrobial populations provide a substantial and broad spectrum reduction in microorganism populations quickly and without problems associated with toxicity and skin irritation.

In particular, antimicrobial cleansing compositions typically contain an active antimicrobial agent, an anionic surfactant for cleansing and foam generation, skin conditioning agents for cosmetic effects, and dyes, perfumes, and optional thickening agents, such as clays, polymers, cellulosic derivatives, or colloids, for aesthetic effects, all in an aqueous carrier.

Several different classes of antimicrobial agents have been used in antimicrobial cleansing compositions. These include active ingredients selected from the following classes: phenolic compounds, carbanalide compounds, lower alcohols, surface active agents halogens, and carboxylic acids. Each of these classes has their own unique advantages and challenges. Examples of specific antimicrobial agents include PCMX (para-chlorometa xylenol), Triclosan, Triclocarban, benzyl alcohol, quaternary ammonium compounds (QAC), iodine and iodine complexes and biguanides (e.g., chlorhexidine digluconate). At this time Triclosan is the dominant antimicrobial active ingredient in the dermal cleanser market.

Although there is an increasing consumer demand for products which have both an activity against bacteria and other microorganisms, there is an even greater demand to fulfill the consumer's expectations with regard to their level of concern with certain biocides such as Triclocarban and Triclosan.

Triclosan is disfavored as an antimicrobial agent due to environmental persistence and health concerns due to the possible formation of intermediate and/or environmental byproducts. Thus, a need exists for an efficacious antimicrobial personal care composition which is substantially free of biocides such as Triclocarban and Triclosan but that still provides a high foam level desired by consumers and is mild to the skin. The present invention is directed to such antimicrobial compositions.

The above-mentioned disadvantages of current antimicrobial compositions are addressed by embodiments of the present invention and will be understood by reading and studying the following specification. The following summary is made by way of example and not by way of limitation. It is merely provided to aid the reader in understanding some of the aspects of the invention.

SUMMARY OF THE INVENTION

In accordance with the present invention, a composition that exhibits rapid cidal efficacy and high foaming attributes is provided. The antimicrobial composition comprises a cationic active ingredient, a foam boosting surfactant which may encompass nonionic surfactants, cationic surfactants or amphoteric surfactants, a novel foam boosting copolymer, a chelating agent, a foam stabilizer and water. The present antimicrobial compositions are free of the antimicrobial agent triclosan (i.e., 2,4,4'-trichloro-2'hydroxy-diphenylether), anionic surfactants and $C_1$ to $C_4$ alcohols and have rapid cidal efficacy. The compositions also provide stable copious foam and may optionally contain ingredients to increase skin compatibility and skin health.

Accordingly, one aspect of the present invention is to provide an antimicrobial composition for reducing microbial population on dermal tissue, the antimicrobial composition comprising: (a) about 0.1 wt. % to about 10.0 wt. %, by weight of cationic actives; (b) about 0.1 wt. % to about 20 wt. %, by weight of a foam boosting surfactant; (c) about 0.5 wt. % to about 25 wt. % dermal adjuvants (d) about 0.05 wt. % to about 12.0 wt. %, by weight of a foam boosting polymer, (e) about 0.1 wt. % to about 10 wt. % of a foam stabilizer, (f) from about 0.1 wt. % about 6.0 wt. % of a chelating agent such that the chelating agent forms a calcium-chelating agent complex with a stability constant (expressed in logarithmic form) greater than 5.5 and (g) water or other suitable diluent wherein the composition it essentially free of triclosan, anionic surfactants and $C_1$ to $C_4$ alcohols.

Another aspect of the present invention is to provide an antimicrobial composition for reducing microbial population on dermal tissue which is stable and has a pH of about 4.0 to about 9.0. The present composition also exhibits excellent esthetic properties, such as copious foam and foam stability and may optionally contain ingredients to increase skin compatibility and skin health. Moreover, the composition may exhibit reduced tissue irritancy potential.

A further aspect of the present invention is to provide personal use products based on an antimicrobial composition of the present invention, for example, a skin cleanser, a surgical scrub, a hand sanitizer gel, a disinfectant, antiseptic wash, and the like.

A further aspect of the present invention is to provide a method of reducing gram positive and/or gram negative bacteria populations on mammalian tissue, including human tissue, by contacting the tissue, like the dermis, with a composition of the present invention for a sufficient time, such as about 15 seconds to 5 minutes, to reduce the bacteria level to a desired level. Antimicrobial efficacy is applicable to viral and fungal organisms as well as gram positive and gram negative bacteria.

While multiple embodiments are disclosed, still other embodiments of the present invention will become apparent to those skilled in the art from the following detailed description, which shows and describes illustrative embodiments of the invention. Accordingly, the detailed description is to be regarded as illustrative in nature and not restrictive.

DETAILED DESCRIPTION OF THE PREFERRED EMBODIMENTS

Figure 1:
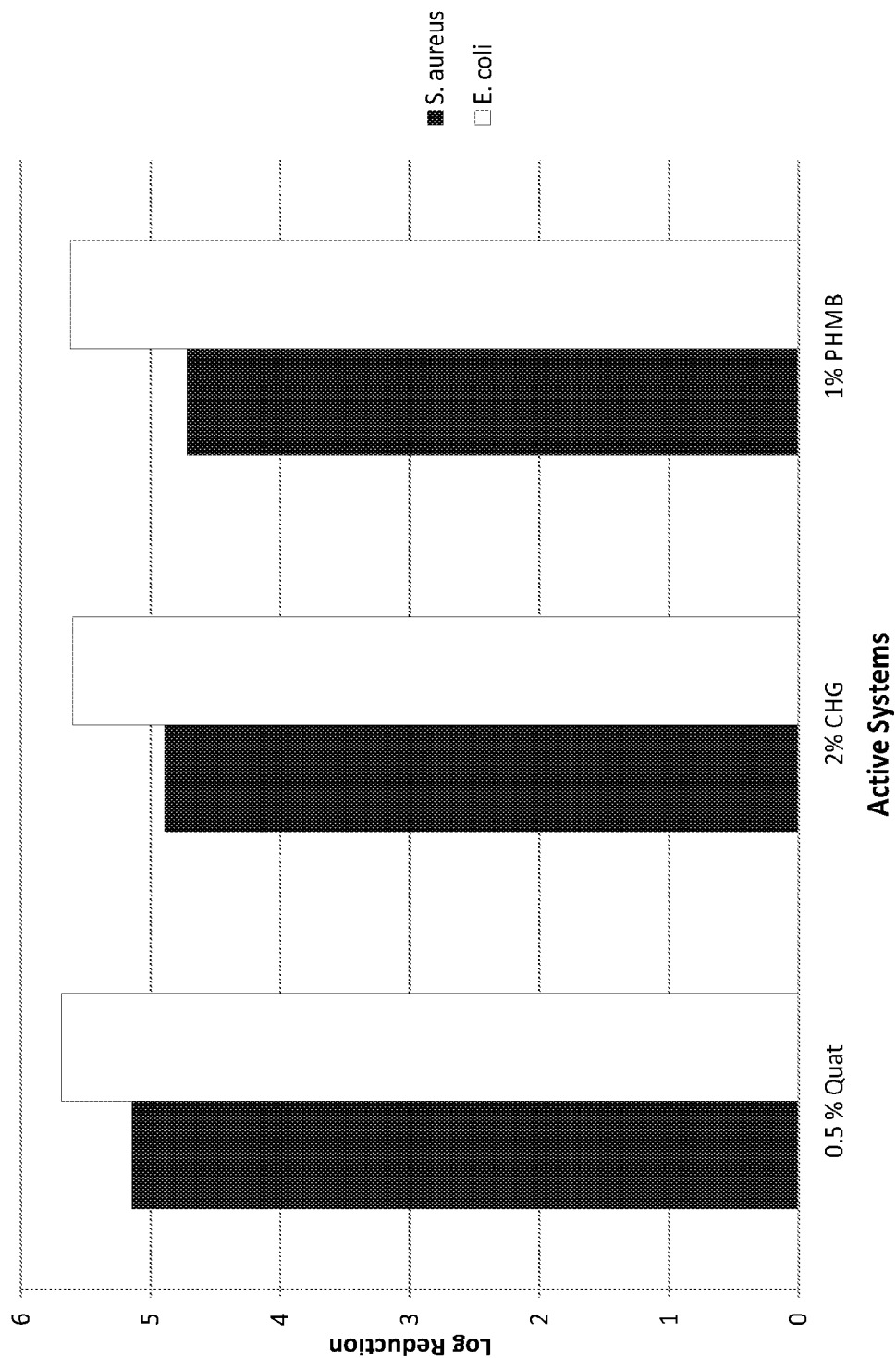
FIG. 1 illustrates a graph depicting the tests results of the efficacy following a 30 second exposure time of three different cationic active ingredients, specifically, 0.5% quat (benzalkonium chloride), 2% CHG (chlorhexidine gluconate), and 1% PHMB (polyhexamethylene biguanide) in a representative surfactant system.

Other than in the operating examples, or where otherwise indicated, all numbers expressing quantities of ingredients or reaction conditions used herein are to be understood as being modified in all instances by the term "about".

As used herein, weight percent (wt-%), percent by weight, % by weight, and the like are synonyms that refer to the concentration of a substance as the weight of that substance divided by the total weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

As used herein, the term "cationic active" is defined as the ingredient that provides antimicrobial cidal activity.

As used herein, the term "skin care active" is defined as the ingredient or ingredients that improve or maintain the health of the dermal barrier.

The term "alkyl" refers to a straight or branched chain monovalent hydrocarbon radical having a specified number of carbon atoms. As used herein, "alkyl" refers to a linear or branched $C_6$-$C_{18}$ carbon chain.

The term "microbial" or "microbial population" refers to bacterial, fungal, yeast, or viral population or combinations thereof or any mixture thereof in a laboratory or natural setting.

The term rapid cidal efficacy refers to ≥3 log kill in up to 60 seconds in the in vitro time kill test ASTM E 2315.

The term "surfactant" or "surface active agent" refers to an organic chemical that when added to a liquid changes the properties of that liquid at a surface or interface.

"Cleansing" means to perform or aid in soil removal, bleaching, microbial population reduction, rinsing, or combination thereof.

As used herein, the term "free" refers to compositions completely lacking the component or having such a small amount of the component that the component does not affect the effectiveness of the composition. The component may be present as an impurity or as a contaminant and shall be less than 0.5 wt. %. In another embodiment, the amount of the component is less than 0.1 wt. % and in yet another embodiment, the amount of component is less than 0.01 wt. %.

It should be noted that, as used in this specification and the appended claims, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The term "actives" or "percent actives" or "percent by weight actives" or "actives concentration" are used interchangeably herein and refers to the concentration of those ingredients involved in cleansing expressed as a percentage minus inert ingredients such as water or salts.

As used herein, the terms "triclosan free" or "free of triclosan" refers to a composition, mixture, or ingredients that do not contain triclosan (2,4,4'-trichloro-2'hydroxydiphenylether) or triclosan containing compounds or to which the same has not been added. Should triclosan or triclosan containing compounds be present through contamination of a composition, mixture, or ingredients, the amount of the same shall be less than 0.5 wt. %. In another embodiment, the amount of is less than 0.1 wt. % and in yet another embodiment, the amount is less than 0.01 wt. %.

Antimicrobial Compositions Containing Cationic Active Compounds

The present invention relates to an antimicrobial composition that exhibits rapid cidal antimicrobial efficacy and high foaming attributes. The antimicrobial composition comprises a cationic active ingredient, a foam boosting surfactant which may encompass anionic surfactants, nonionic surfactants, amphoteric surfactants, or cationic surfactants and water. The present antimicrobial compositions are free of the antimicrobial agent triclosan (i.e., 2,4,4'-trichloro-2'hydroxy-diphenylether), anionic surfactants and $C_1$ to $C_4$ alcohols, has rapid cidal efficacy and provide stable copious foam and may optionally contain ingredients to increase skin compatibility and skin health.

In one embodiment, an antimicrobial composition for reducing microbial population on dermal tissue includes: (a) about 0.1 wt. % to about 10.0 wt. %, by weight of cationic actives; (b) about 0.1 wt. % to about 20 wt. %, by weight of a foam boosting surfactant; (c) about 0.5 wt. % to about 25 wt. % dermal adjuvants and (d) water or other suitable diluent.

Another aspect of the present invention is to provide an antimicrobial composition for reducing microbial population on dermal tissue which is stable and has a pH of about 5.0 to about 8.0. The present composition also surprisingly exhibits excellent esthetic properties, such as copious foam and foam stability and may optionally contain ingredients to increase skin compatibility and skin health. Moreover, the composition may exhibit reduced tissue irritancy potential.

A further aspect of the present invention is to provide personal use products based on an antimicrobial composition of the present invention, for example, a skin cleanser, a surgical scrub, a hand sanitizer gel, a disinfectant, and the like.

A further aspect of the present invention is to provide a method of reducing gram positive and/or gram negative bacteria populations on mammalian tissue, including human tissue, by contacting the tissue, like the dermis, with a composition of the present invention for a sufficient time, such as about 30 seconds to 5 minutes, to reduce the bacteria level to a desired level.

The following illustrates non-limiting embodiments of the present invention.

Cationic Actives

A cationic active is present in an antimicrobial composition for reducing microbial population on the dermal tissue of a mammal of the present invention in an amount of about 0.1 wt. % to about 10.0 wt. %, and preferably about 0.1 wt. % to about 5.0 wt. %, by weight of the composition.

The amount of antimicrobial agent in the composition is related to the end use of the composition, The amount of antimicrobial agent is sufficient in the compositions of the invention to achieve a microbial kill in a short contact time, for example, 15 to 30 seconds.

Cationic active ingredients are an antimicrobial agent useful in the present invention. The cationic or cationically-active ingredients are substances based on nitrogen centered cationic moieties with net positive change. The cationic or cationically-active ingredients are preferably selected from the group consisting of cationic polymers, cationic surfactants, cationic monomers, cationic silicon compounds, cationic derivatized protein hydrolyzates and betaine with at least one cationic or cationically-active group.

Suitable cationic active ingredients contain quaternary ammonium groups. Suitable cationic active ingredients especially include those of the general formula:

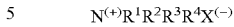

$$N^{(+)}R^1R^2R^3R^4X^{(-)}$$

wherein $R^1$, $R^2$, $R^3$ and $R^4$ independently of each other represent alkyl groups, aliphatic groups, aromatic groups, alkoxy groups, polyoxyalkylene groups, alkylamido groups, hydroxyalkyl groups, aryl groups, $H^+$ ions, each with from 1 to 22 carbon atoms, with the provision that at least one of the groups $R^1$, $R^2$, $R^3$ and $R^4$ has at least eight carbon atoms and wherein X(−) represents an anion, for example, a halogen, acetate, phosphate, nitrate or alkyl sulfate, preferably a chloride. The aliphatic groups can also contain cross-linking or other groups, for example additional amino groups, in addition to the carbon and hydrogen atoms.

Particular cationic active ingredients include, for example, but are not limited to, alkyl dimethyl benzyl ammonium chloride (ADBAC), alkyl dimethyl ethylbenzyl ammonium chloride, dialkyl dimethyl ammonium chloride, benzethonium chloride, N,N-bis-(3-aminopropyl)dodecylamine, chlorhexidine gluconate, an organic and/or organic salt of chlorhexidine gluconate, PHMB (polyhexamethylene biguanide), salt of a biguanide, a substituted biguanide derivative, an organic salt of a quaternary ammonium containing compound or an inorganic salt of a quaternary ammonium containing compound or mixtures thereof.

In accordance with an important feature of the present invention, a present antimicrobial composition is substantially free of triclosan. The phrase "substantially free" of triclosan is defined as meaning that the composition contains 0% to about 0.25% by weight, in total, of triclosan. In particular, triclosan may be present in an antimicrobial composition in a total amount of 0.25% or less either as a by-product or as a component of an ingredient in the composition, but triclosan is not intentionally introduced into the composition.

Triclosan is disfavored as an antimicrobial agent due to environmental and health concerns due to the possible formation of intermediate and/or environmental by products.

Foam-Boosting Surfactant

In addition to an antimicrobial agent, and a quaternized sugar-derived surfactant the present antimicrobial composition for reducing microbial population on the dermal tissue of a mammal of the present invention also contains one or more foam boosting surfactants. The one or more foam booting surfactants is present in an amount of about 0.1% to about 40.0%, and preferably about 1% to about 25%, by weight, of the composition.

The amount of foam boosting surfactant present in the composition is related to the amount of the cationic active in the composition, the amount of the quaternized sugar-derived surfactant in the composition, the identity of the foam boosting surfactant, and the end use of the composition.

The foam-boosting surfactant can be (a) nonionic surfactants or cationic surfactants, or mixtures thereof. The formulation is essentially free of anionic or zwitteronic surfactants.

Non Ionic Foam Boosting Surfactant

Examples of non ionic foam-boosting co-surfactants include, but are not limited to, alkyl amine oxide, alkyl ether amine oxide, alkyl alcohol alkoxylates, aryl alcohol alkoxylates, substituted alcohol alkoxylates, block nonionic copolymers, heteric nonionic copolymers, alkanolamides, substituted amides, or polyethoxylated glycerol derivatives.

The antimicrobial composition can contain a nonionic surfactant component that includes a detersive amount of nonionic surfactant or a mixture of nonionic surfactants. Typically, a nonionic surfactant has a hydrophobic region, such as a long chain alkyl group or an alkylated aryl group, and a hydrophilic group comprising an ethoxy and/or other hydrophilic moieties. As defined herein, a "nonionic foam-boosting surfactant" has a hydrophobic region having an alkyl group containing six to eighteen carbon atoms, and an average of one to about twenty ethoxy and/or propoxy moieties. Examples of non ionic foam-boosting co-surfactants include, but are not limited to, alkyl amine oxide, alkyl ether amine oxide, alkyl alcohol alkoxylates, aryl alcohol alkoxylates, substituted alcohol alkoxylates, block nonionic copolymers, heteric nonionic copolymers, alkanolamides, or polyethoxylated glycerol esters, and mixtures thereof.

Numerous other nonionic surfactants are disclosed in McCutcheon's Detergents and Emulsifiers, 1993 Annuals, published by McCutcheon Division, MC Publishing Co., Glen Rock, N.J., pp. 1-246 and 266-273; in the *CTFA International Cosmetic Ingredient Dictionary, Fourth Ed.*, Cosmetic, Toiletry and Fragrance Association, Washington, D.C. (1991) (hereinafter the *CTFA Dictionary*) at pages 1-651; and in the *CTFA Cosmetic Ingredient Handbook, First Ed.*, Cosmetic, Toiletry and Fragrance Association, Washington, D.C. (1988) (hereafter the *CTFA Handbook*), at pages 86-94, each incorporated herein by reference.

Amphoteric Foam Boosting Surfactant

The antimicrobial composition can contain an amphoteric surfactant component that includes a detersive amount of amphoteric surfactant or a mixture of amphoteric surfactants. Suitable amphoteric surfactants that can be used include, but are not limited to, imidiazolines and imidiazoline derivatives, isethionates, betaine derivatives, amphoacetate derivatives, propionates, and mixtures thereof.

Cationic Foam Boosting Surfactant

The antimicrobial composition may contain a cationic surfactant component that includes a detersive amount of cationic surfactant or a mixture of cationic surfactants. Cationic surfactants that can be used in the antimicrobial composition include, but are not limited to, quaternized sugar-derived surfactants, quaternized polysaccharides, alkyl polysaccharides, alkoxylated amines, alkoxylated ether amines, phospholipids, phospholipid derivatives, and mixtures thereof. Particularly preferred is a quaternized sugar-derived surfactant. The quaternized sugar surfactant may be present in an amount of about 0.1% to about 18%, and preferably about 0.25% to about 12.5%, by weight, of the composition.

The amount of quaternized sugar-derived surfactant present in the composition is related to the amount of the cationic active in the composition, to the identity of the quaternized sugar-derived surfactant, and the end use of the composition.

The quaternized sugar-derived surfactant is a quaternized alkyl polyglucoside or a polyquaternized alkyl polyglucoside, and the like.

In one embodiment, the antimicrobial composition of the present invention includes a polyquaternary functionalized alkyl polyglucoside, a cationic active ingredient, water, and an optional foam boosting surfactant. The poly quaternary functionalized alkyl polyglucoside is a cationic surfactant naturally derived from alkyl polyglucosides and has a sugar backbone. Poly quaternary alkyl polyglucosides have the following representative formula:

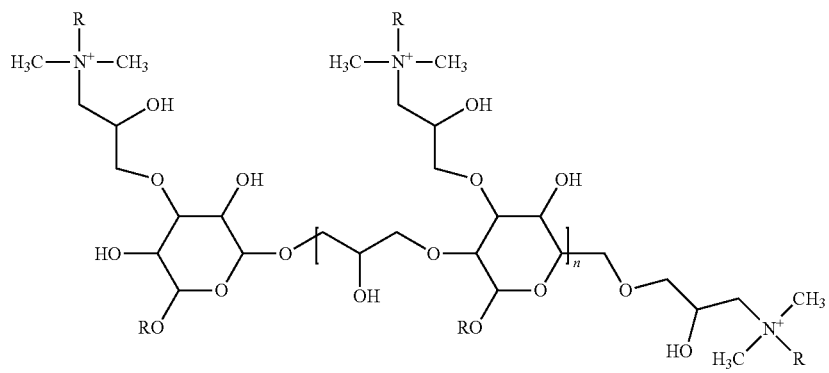

Wherein R is an alkyl group having from about 6 to about 22 carbon atoms and n is an integer ranging from 4 to 6. Examples of suitable poly quaternary functionalized alkyl polyglucosides components which can be used in the cleansing compositions according to the present invention include those in which the R alkyl moiety contains from about 8 to about 12-carbon atoms. In a preferred embodiment the quaternary functionalized alkyl polyglucoside contains primarily about 10-12 carbon atoms. Examples of commercially suitable poly quaternary functionalized alkyl polyglucosides useful in cleansing compositions of the present invention include but is not limited to: Poly Suga® Quat series of quaternary functionalized alkyl polyglucosides, available from Colonial Chemical, Inc., located in South Pittsburg, TN.

In another embodiment, the antimicrobial composition of the present invention includes a quaternary functionalized alkyl polyglucoside, a cationic active ingredient, water, and an optional foam boosting surfactant. The quaternary functionalized alkyl polyglucoside is a naturally derived cationic surfactant from alkyl polyglucosides and has a sugar backbone. Quaternary functionalized alkyl polyglucosides have the following representative formula:

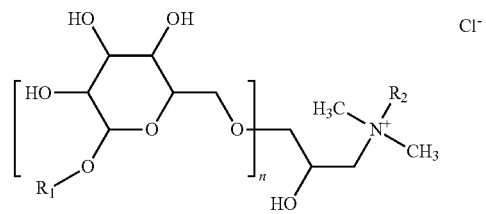

Wherein $R_1$ is an alkyl group having from about 6 to about 22 carbon atoms, and $R_2$ is $CH_3(CH_2)_{n'}$ where n' is an integer ranging from 0-21. Examples of suitable quaternary functionalized alkyl polyglucosides components which can be used in the cleansing compositions according to the present invention include those in which the $R_1$ alkyl moiety contains primarily about 10-12 carbon atoms, the $R_2$ group is $CH_3$ and n is the degree of polymerization of 1-2. Further examples of a suitable quaternary functionalized alkyl polyglucoside include, but are not limited to, the antimicrobial and antifungal quaternary functionalized alkyl polyglucosides described in U.S. Pat. Nos. 7,084,129 and 7,507,399 the disclosures of which are hereby incorporated by reference. Examples of commercially suitable quaternary functionalized alkyl polyglucosides useful in cleansing compositions of the present invention include but is not limited to: Suga® Quat TM 1212 (primarily $C_{12}$ quaternary functionalized alkyl polyglucoside), Suga® Quat L 1210 (primarily $C_{12}$ quaternary functionalized alkyl polyglucoside), and Suga® Quat S 1218 (primarily $C_{12}$ quaternary functionalized alkyl polyglucoside) available from Colonial Chemical, Inc., located in South Pittsburg, TN Dermal Adjuvant/Skin Care Active The composition can contain from about 1 wt. % to about 30 wt. % of dermal adjuvants, preferably from about 5 wt. % to about 25 wt. % of dermal adjuvants. Dermal adjuvants/skin care actives generally include any substance which improves or maintains the health of the dermal barrier. Some examples include but are not limited to emollients and skin moisturizer/protectants.

1) Emollients

The composition can include emollients which are polymers such as dimethyl siloxanes Examples of high include but are not limited to dicaprylyl carbonate, dibutyl adipate, hexyl laurate, dicaprylyl ether, propylheptyl caprylate, 4-10 centistoke silicone oil, D4, 5, or 6 cyclic siloxane, isocetyl palmitate, hydrogentated polyisobutene, and diethylhexylcarbonate polymers such as dimethyl siloxanes examples include capric/caprylic triglyceride, C12-15 alkyl benzoate, capric triglyceride, caprylic triglyceride, isopropyl myristrate, isopropyl palmitate, octyldodecanol, decyl oleate, cocoglycerides, ethylhexyl stearate, ceteraryl isononanoate, cetearyl ethyhexanonate, decyl cocoate, cetyl dimethicone, ethylhexyl palmitate, PPG-11 stearyl ether, PPG-15 stearyl ether, Dimethicone fluid, and PPG-14 butyl ether.

These materials also may include polymers such as siloxanes examples include mono-, di-, and tri-glycerides and butters and hydrogenated versions of seed and nut oils including but not limited to; palm oil, coconut oil, vegetable oil, avocado oil, canola oil, corn oil, soy bean oil, sunflower oil, safflower oil, meadowfoam seed oil, bilberry seed oil, watermelon seed oil, olive oil, cranberry, macadamia nut oil, argan oil, pomegranate oil, argan moraccan oil, blue berry oil, raspberry oil, walnut oil, pecan oil, peanut oil, bayberry oil, mango seed oil, Manila oil, castor oil: Shea butter, jojoba oil, hydrolyzed jojoba oil, Carnauba butter, Carnauba wax, castor isostearate succinate stearyl heptanoate, cetyl ricinoleate, oleyl frucate, sucrose monostearate, sucrose distearate, sucrose tristearate, sucrose tetrastearate, candela wax, soybean wax, Rapeseed wax, palm wax, bees wax, petrolatum, myristyl myristate, Oleyl Erucate, squalane, stearyl alcohol, Cetearyl isononanoate, polyisobutene, glyceryl stearate, glyceryl distearate, cetyl alcohol, lanolin, lanolin ethoxylate, low molecular weight polyethylene waxes, lower molecular weight polypropylene waxes, PEG-30 glyceryl cocoate, PEG-80 Glyceryl cocoate, PEG-30 Glyceryl stearate, PEG-8 Ricinoleate, PEG-8 Raspberriate, Linear (otherwise known as bis) and Pendent versions of including hydroxyl terminated and methyl ether terminated; PEG-3 to PEG-32 Dimethicone (including but not limited to: PEG-3 Dimethicone, PEG-8 Dimethicone, PEG-9 Dimethicone, PEG-10 Dimethicone, PEG-11 Methyl ether dimethicone, PEG-12 Dimethicone, PEG-14 Dimethicone, PEG-17 Dimethicone, PEG-32 Dimethicone), bis-PEG/PPG-20/20 Dimethicone, PEG/PPG 20/23 Dimethicone, PEG/PPG 20/22 Butyl Ether Dimethicone, PEG/PPG 23/6 Dimethicone, PEG/PPG 20/15 Dimethicone.

Alkyl modified dimethicone (stearoxy dimethicone, behenoxy dimethicone, cetyl dimethicone, certeryl methicone C30-45 Alkyl cetearyl dimethicone copolymer, C30-45 Alkyl dimethicone, caprylyl methicone, PEG-8 dimethicone/dimer dilinoleic acid copolymer, Bis-PEG-10 Dimethicone/Dimer Dilinoleate Copolymer, Stearoxymethicone/Dimethicone Copolymer, Dipheyl dimethicone, Lauryl polyglycerol-3 polydimethylsiloxyethyl dimethicone, Lauryl PEG-9 polydimethylsiloxyethyl dimethicone), Dimethicone fluid (>20cst), quaternized ammonia silicone polymers, Amino silicones, silicone quaternium-18, Amodimethicone, phenyltrimethicone, amino silicone polyethers, Polyglycerol-3 Disiloxane dimethicone, Polyglycerol-3 polydimethylsiloxyethyl dimethicone, and PEG-9 polydimethylsiloxyethyl dimethicone.

Emollients, if present may be in an amount of from about 0.01 wt. % to about 10 wt. %, preferably from about 0.05 wt. % to about 8 wt. % and more preferably from about 0.1 wt. % to about 5 wt. %.

2) Skin Moisturizer/Protectant

The composition can include at least one additional skin conditioner such as vitamins, a humectant, an occlusive agent, or other moisturizer to provide skin moisturizing, skin softening, skin barrier maintenance, anti-irritation, or other skin health benefits. Some non-limiting examples of additional skin conditioners include alkyl benzoate, myristyl myristate, cetyl myristate, gelatin, carboxylic acid, lactic acid, glyceryl dioleate, methyl laurate, PPG-9 laurate, lauryl lacylate allantoin, octyl palmitate, lanolin, propylene glycol, butylene glycol, ethylene glycol, caprylyl glycol, monobutyl ether, glycerine, fatty acids, proline, natural oils such as almond, mineral, canola, sesame, soybean, pyrrolidine, wheat germ, hydrolyzed wheat protein, hydrolyzed oat protein, hydrolyzed collagen, corn, peanut and olive oil, isopropyl myristate, myristyl alcohol, aloe vera, algae extract, gluconic acid, hydrolyzed silk protein, 1,3-propane-diol, Vitamin E, nicatinamide, stearyl alcohol, isopropyl palmitate, sorbitol, amino acid complexes, panthenol, allantoin, Dihydroxypropyltrimonium Chloride, quaternized hydrolyzed protein such as collagen, oat, wheat, etc . . . , inositol, fructose, sucrose, hydrolyzed plant proteins, seaweed extract, polyethylene glycol, ammonium lactate, sodium hyaluronate, and cyclic peptides.

Some non-limiting examples of humectants include hydroxyethyl urea, agarose, urea, sodium PCA, arginine PCA, fructose, glucose, glutamic acid, glycerine, honey, lactose, maltose, polyethylene glycol, sorbitol and mixtures thereof.

Some non-limiting examples of occlusive agents include petrolatum, shea butter, avocado oil, balm mint oil, cod liver oil, mineral oil, trimyristin, stearyl stearate, synthetic wax, or mixtures thereof. Some non-limiting examples of other moisturizers include ethyl hexylglycerin, cholesterol, cystine, hyaluronic acid, keratin, lecithin, egg yolk, glycine, PPG-12, polyquaternium polymers such as polyquaternium-11, behentrimonium chloride, dihydroxypropyl PEG-5 linoleammonium chloride, glycerol oleate, PEG-7 glyceryl cocoate, cocoglucoside, PEG-200 hydrogenated glyceryl palmate, panthenol, retinol, salicylic acid, vegetable oil, methyl gluceth-10, methyl gluceth-20, ethoxylated derivatives of skin conditioners such as glycereth-26 and ethoxylated shea butter, and mixtures thereof. Finally, some non-limiting examples of anti-irritants include bisabolol and panthenol.

The skin conditioner component is present in lower amounts that seen in traditional commercial skin sanitizers. Applicants have found that due to the chronic use of such sanitizers, lower amounts can be used with similar health benefits and less tacky residue. The skin conditioner or combination thereof in total is present in the composition in an amount from about 0.1 wt. % to about 20 wt. %, preferably from about 0.5 wt. % to about 15 wt. %, and more preferably from about 1 wt. % to about 10 wt. %.

Foam Boosting Copolymer

The composition of the invention includes a novel foam boosting polymer. The foam boosting polymer is present in an amount of from about 0.05 wt. % to about 18 wt. %, preferably from about 0.1 to about 10 wt. %.

Polymers which function according to the invention comprise a hydrophobically modified cationic polymer obtainable from the polymerization of the following structural units:
(i) a first structural unit derived from one or more cationic ethylenically unsaturated monomers;
(ii) a second structural unit derived from one or more water-soluble monomers.

(i) First Structural Unit

The first structural unit is a water-soluble cationic ethylenically unsaturated monomer. The first structural unit can be a dialkyl diallyl ammonium with halides, hydrogensulfate or methosulfate as counterions according to formula (I):

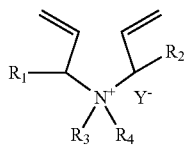
(I)

wherein:
$R_1$ and $R_2$ are, independently of one another, hydrogen or $C_1$-$C_4$ alkyl;
$R_3$ and $R_4$ are, independently of one another, hydrogen, alkyl, hydroxyalkyl, carboxyl alkyl, carboxyamide alkyl or alkoxyalkyl groups having from 1 to 18 carbon atoms; and
Y— is the counterion selected from the group consisting of chloride, bromide, iodine or hydrogensulfate or methosulfate.

In another embodiment, the first structural unit is a quaternary or acid salt of dialkyl amino alkyl (meth)acrylate. In a further embodiment, the first structural unit is an acid salt of a dialkyl amino alkyl (meth) acrylamide or a quaternary dialkyl amino alkyl (meth) acrylamide according to formula (II):

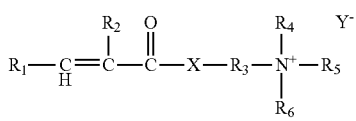
(II)

wherein:
$R_1$ is H or $C_1$-$C_4$ alkyl;
$R_2$ is H or methyl;
$R_3$ is $C_1$-$C_4$ alkylene;
$R_4$, $R_5$ and $R_6$ are each independently H or $C_1$-$C_{30}$ alkyl;
X is —O— or —NH—; and
Y is Cl; Br; I; hydrogensulfate or methosulfate.

In one embodiment of the present invention, it is preferred that, in the cationic monomer of the formula (II), wherein:
$R_1$ and $R_2$ are each H or
$R_1$ is H and $R_2$ is $CH_3$ or preferably also H.

Suitable examples of the first structural unit are diallyl dimethyl ammonium chloride (DADMAC), (3-acrylamidopropyl)-trimethylammonium chloride (APTAC), (3-methacryl-amidopropyl)-trimethylammonium chloride (MAPTAC), dimethylaminopropylacrylat methochlorid, dimethylaminopropylmethacrylat methochlorid. Further suitable examples of the first structural unit are [2-(Acryloyloxy)ethyl]trimethylammonium chloride, also referred to as dimethylaminoethyl acrylate methochloride (DMA3*MeCl), or trimethyl-[2-(2-methylprop-2-enoyloxy)ethyl]azanium chloride, also referred as dimethylaminoethyl methacrylate methochloride (DMAEMA*MeCl). Preferably, the first structural unit is DADMAC.

(ii) Second Structural Unit

The second structural unit is acylamide or methacrylamide

All wt % for each of the structural units are calculated based on 100% by weight of all structural units derived from all the monomers in the co polymer. A preferred copolymer is a DADMAC/(meth)acrylamide copolymer with a molecular weight of approximately 2,000,000 such as the Mackermium 007 line of copolymers available from Rhodia, Inc.

Foam Stabilizer

The composition includes a foam solubilizer which includes an organic solvent, other than a short chain alcohol, typically soluble in both water and oil. Examples of foam solubilizers according to the present invention include: polyols, such as glycerol (glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, other glycols, sulfoxides, such as dimethylsulfoxide (DMSO), dimethylformamide, methyl dodecyl sulfoxide, dimethylacetamide; monooleate of ethoxylated glycerides (with 8 to 10 ethylene oxide units); azone (1-dodecylazacycloheptan-2-one), 2-(n-nonyl)-1,3-dioxolane; esters, such as isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, such as acetamide oleates such as triolein; various alkanoic acids such as caprylic acid; lactam compounds, such as azone; alkanols, such as dialkylamino acetates, and admixtures thereof. According to one preferred embodiment the foam solubilizer is hexalene glycol.

The foam solubilizer is present in the composition in an amount of from about 0.1 wt. % to about 10 wt. %, preferably from about 0.5 wt. % to about 8 wt. %.

Chelating Agent

The composition is generally a concentrate or a ready to use composition that includes a chelating agent. In general, a chelating agent is a molecule capable of coordinating (i.e., binding) the metal ions commonly found in water sources to prevent the metal ions from interfering with the action of the other ingredients. Examples of chelating agents include phosphonic acid and phosphonates, phosphates, aminocarboxylates and their derivatives, pyrophosphates, ethylenediamine and ethylenetriamine derivatives, hydroxyacids, and mono-, di-, and tri-carboxylates and their corresponding acids. In certain embodiments the composition is phosphate free. Preferred chelating agents form calcium-chelating agent complexes with a stability constant (expressed in logarithmic form) of about 5.5 or greater. The calcium-chelating agent stability constant (K) is the measure of the stability of a calcium-chelating agent complex (CaL) formed by the reaction of a calcium ion (Ca) with a chelating agent (L) in aqueous solution.

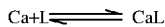

The stability constant is expressed as:

$$K = \frac{[CaL]}{[Ca][L]}$$

Where:
K=stability constant for the calcium-chelating agent complex
[CaL]=concentration (mol/L) of the calcium-chelating agent complex
[Ca]=concentration (mol/L) of calcium ions
[L]=concentration (mol/L) of the chelating agent Preferred chelating agents are selected from the group comprising ethylenediaminetetraacetic acid (EDTA); diethylenetriaminepentacetic acid (DTPA); methylglycine-N,N-diacetic acid (MGDA); glutamic acid-N,N-diacetic acid (GLDA); Aspartic acid-N,N-diacetic acid (ASDA) and alkali, alkali earth metal, transition metal and/or ammonium salts thereof.

Carriers

The carrier of the present antimicrobial composition comprises water, propylene glycol, glycerols, alcohols or mixtures thereof. It should be appreciated that the water may be provided as deionized water or as softened water. The water provided as part of the composition can be relatively free of hardness. It is expected that the water can be deionized to remove a portion of the dissolved solids. That is, the concentrate can be formulated with water that includes dissolved solids, and can be formulated with water that can be characterized as hard water.

The antimicrobial composition of the present invention does not rely upon a low pH or a high pH to provide a rapid reduction in microbial populations. Antimicrobial populations of the present invention have a pH of about 5.0 to about 8.0. Within this pH range, the present compositions effectively reduce microbial populations, and are consumer acceptable, i.e., are mild to the skin, are phase stable, and generate copious, stable foam.

Additional Functional Materials

The antimicrobial composition can include additional components or agents, such as additional functional materials. As such, in some embodiments, the antimicrobial composition including the cationic active ingredients and quaternary sugar-derived surfactants may provide a large amount, or even all of the total weight of the antimicrobial composition, for example, in embodiments having few or no additional functional materials disposed therein. The functional materials provide desired properties and functionalities to the antimicrobial composition. For the purpose of this application, the term "functional materials" include a material that when dispersed or dissolved in a use and/or concentrate solution, such as an aqueous solution, provides a beneficial property in a particular use. The antimicrobial composition containing the cationic active ingredients and the quaternized sugar-derived surfactants may optionally contain additional surfactants, pH adjusting compound, preservatives, antioxidants, fragrances, dyes, other disinfectants, sanitizers, thickening or gelling agents, or mixtures thereof. Some particular examples of functional materials are discussed in more detail below, but it should be understood by those of skill in the art and others that the particular materials discussed are given by way of example only, and that a broad variety of other functional materials may be used. For example, may of the functional material discussed below relate to materials used in disinfecting and/or cleansing applications, but it should be understood that other embodiments may include functional materials for use in other applications.

Preservatives

The composition may optionally include a preservative. Generally, preservatives fall into specific classes including phenolics, halogen compounds, quaternary ammonium compounds, metal derivatives, amines, alkanolamines, nitro derivatives, biguanides, analides, organosulfur and sulfur-nitrogen compounds, alkyl parabens, and miscellaneous compounds. Some non-limiting examples of phenolic antimicrobial agents include pentachlorophenol, orthophenylphenol, chloroxylenol, p-chloro-m-cresol, p-chlorophenol, chlorothymol, m-cresol, o-cresol, p-cresol, isopropyl cresols, mixed cresols, phenoxyethanol, phenoxyethylparaben, phenoxyisopropanol, phenyl paraben, resorcinol, and derivatives thereof. Some non-limiting examples of halogen compounds include trichlorohydroxy diphenyl ether (Triclosan), sodium trichloroisocyanurate, sodium dichloroisocyanurate, iodine-poly(vinylpyrolidin-onen) complexes, and bromine compounds such as 2-bromo-2-nitropropane-1,3-diol, and derivatives thereof. Some non-limiting examples of quaternary ammonium compounds include benzalkonium chloride, benzethonium chloride, behentrimonium chloride, cetrimonium chloride, and derivatives thereof. Some non-limiting examples of amines and nitro containing compounds include hexahydro-1,3,5-tris(2-hydroxyethyl)-s-triazine, dithiocarbamates such as sodium dimethyldithiocarbamate, and derivatives thereof. Some non-limiting examples of biguanides include polyaminopropyl biguanide and chlorhexidine gluconate. Some non-limiting examples of alkyl parabens include methyl, ethyl, propyl and butyl parabens.

The preservative is preferably present in the composition in an amount from about 0 to about 3 wt. %, from about 0.01 to about 2 wt. %, and from about 0.5 to about 1 wt. %.

Thickener

The composition may optionally include a thickener. Exemplary thickeners include (1) cellulosic thickeners and their derivatives, (2) natural gums, (3) starches, (4) stearates, and (5) fatty acid alcohols, (6) acrylic acid polymers and crosspolymers (example "carbomer", (7) Aristoflex AVC (need generic category name) Some non-limiting examples of cellulosic thickeners include carboxymethyl hydroxyethylcellulose, cellulose, hydroxybutyl methylcellulose, hydroxyethylcellulose, hydroxypropylcellulose, hydroxypropyl methyl cellulose, methylcellulose, microcrystalline cellulose, sodium cellulose sulfate, and the like. Some non-limiting examples of natural gums include acacia, calcium carrageenan, guar, gelatin, guar gum, hydroxypropyl guar, karaya gum, kelp, locust bean gum, pectin, sodium carrageenan, tragacanth gum, xanthan gum, and the like. Some non-limiting examples of starches include oat flour, potato starch, wheat flour, wheat starch, and the like. Some non-limiting examples of stearates include PEG-150 distearate, methoxy PEG-22/dodecyl glycol copolymer, and the like. Some non-limiting examples of fatty acid alcohols include caprylic alcohol, cetearyl alcohol, lauryl alcohol, oleyl alcohol, palm kernel alcohol, and the like.

The amount of thickener in the composition depends on the desired viscosity of the composition.

Additional Surfactants

The composition may optionally contain additional surfactant or combination of surfactants. These can be selected from water soluble or water dispersible nonionic, semi-polar nonionic, cationic, amphoteric, or surface-active agents; or any combination thereof. The particular surfactant or surfactant mixture chosen for use in the process and products of this invention can depend on the conditions of final utility, including method of manufacture, physical product form, use pH, and the like. The composition is substantially free of anionic or zwitteronic surfactants.

A typical listing of the classes and species of surfactants useful herein appears in U.S. Pat. No. 3,664,961 issued May 23, 1972, to Norris. The disclosure of which is hereby incorporated by reference. Additional surfactants, if present may be in the amount of from 0.5 to about 10 wt. %, from about 1.0 to about 7 wt. % and from about 2 to about 5 wt. %.

pH-Adjusting Compound

Sanitizer compositions of the present invention have a pH of about 4.0 to about 8. Within this pH range, the present compositions effectively reduce microbial populations, and are consumer acceptable, i.e., are mild to the skin, are phase stable, and generate copious, stable foam. In some instances a pH adjusting compound may be necessary in a sufficient amount to provide a desired composition pH. To achieve the full advantage of the present invention, the pH-adjusting compound is present in an amount of about 0.05% to about 3.5%, by weight.

Examples of basic pH-adjusting compounds include, but are not limited to, ammonia; mono-, di-, and trialkyl amines; mono-, di-, and trialkanolamines; alkali metal and alkaline earth metal hydroxides; alkali metal phosphates; alkali sulfates; alkali metal carbonates; and mixtures thereof. However, the identity of the basic pH adjuster is not limited, and any basic pH-adjusting compound known in the art can be used. Specific, nonlimiting examples of basic pH-adjusting compounds are ammonia; sodium, potassium, and lithium hydroxide; sodium and potassium phosphates, including hydrogen and dihydrogen phosphates; sodium and potassium carbonate and bicarbonate; sodium and potassium sulfate and bisulfate; monoethanolamine; trimethylamine; isopropanolamine; diethanolamine; and triethanolamine.

The identity of an acidic pH-adjusting compound is not limited and any acidic pH-adjusting compound known in the art, alone or in combination, can be used. Examples of specific acidic pH-adjusting compounds are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid.

Antioxidant

The composition may optionally include an antioxidant for improved skin condition through the removal of free radicals, and improved product stability. Some non-limiting examples of antioxidants include retinol and retinol derivatives, ascorbic acid and ascorbic acid derivatives, BHA, BHT, beta carotene, cysteine, erythorbic acid, hydroquinone, tocopherol and tocopherol derivatives, and the like.

If an antioxidant is included, it is preferably present in the composition in an amount from about 0.001 to about 2 wt. %, from about 0.01 to about 1 wt. %, and from about 0.05 to about 0.5 wt. %.

Fragrance

The composition may optionally include a fragrance. Examples of possible fragrances include, but are not limited to natural oils or naturally derived materials, and synthetic fragrances such as hydrocarbons, alcohols, aldehydes, ketones, esters, lactones, ethers, nitriles, and polyfunctionals. Non-limiting examples of natural oils include the following: basil (*Ocimum basilicum*) oil, bay (*Pimento acris*) oil, bee balm (*Monarda didyma*) oil, bergamot (*Citrus aurantium bergamia*) oil, cardamom (*Elettaria cardamomum*) oil, cedarwood (*Cedrus atlantica*) oil, chamomile (*Anthemis nobilis*) oil, cinnamon (*Cinnamomum cassia*) oil, citronella (*Cymbopogon nardus*) oil, clary (*Salvia sclarea*) oil, clove (*Eugenia caryophyllus*) oil, cloveleaf (*Eufenia caryophyllus*) oil, *Cyperus esculentus* oil, cypress (*Cupressus sempervirens*) oil, *Eucalyptus citriodora* oil, geranium maculatum oil, ginger (*Zingiber officinale*) oil, grapefruit (*Citrus grandis*) oil, hazel (*Corylus avellana*) nut oil, jasmine (*Jasminum officinale*) oil, *Juniperus communis* oil, *Juniperus oxycedrus* tar, *Juniperus virginiana* oil, kiwi (*Actinidia chinensis*) water, lavandin (*Lavandula hybrida*) oil, lavender (*Lavandula angustifolia*) oil, lavender (*Lavandula angustifolia*) water, lemon (*Citrus medica limonum*) oil, lemongrass (*Cymbopogon schoenanthus*) oil, lime (*Citrus aurantifolia*) oil, linden (*Tilia cordata*) oil, linden (*Tilia cordata*) water, mandarin orange (*Citrus nobilis*) oil, nutmeg (*Myristica fragrans*) oil, orange (*Citrus aurantium dulcis*) flower oil, orange (*Citrus aurantium dulcis*) oil, orange (*Citrus aurantium dulcis*) water, patchouli (*Pogostemon cablin*) oil, peppermint (*Menthe piperita*) oil, peppermint (*Menthe peperita*) water, rosemary (*Rosmarinus officinalis*) oil, rose oil, rose (*Rosa damascena*) extract, rose (*Rosa multiflora*) extract, rosewood (*Aniba rosaeodora*) extract, sage (*Salvia officinalis*) oil, sandalwood (*Santalum album*) oil, spearmint (*Menthe viridis*) oil, tea tree (*Melaleuca alternifolia*) oil, and ylang ylang (*Cananga odorata*) oil. Some non-limiting examples of synthetic hydrocarbon fragrances include caryophyllene, β-farnesene, limonene, α-pinene, and β-pinene. Some non-limiting examples of synthetic alcohol fragrances include bacdanol, citronellol, linalool, phenethyl alcohol, and α-terpineol (R=H). Some non-limiting examples of synthetic aldehyde fragrances include 2-methyl undecanal, citral, hexyl cinnamic aldehyde, isocycolcitral, lilial, and 10-undecenal. Some non-limiting examples of synthetic ketone fragrances include cashmeran, α-ionone, isocyclemone E, koavone, muscone, and tonalide. Some non-limiting examples of synthetic ester fragrances include benzyl acetate, 4-t-butylcyclohexyl acetate (cis and trans), cedryl acetate, cyclacet, isobornyl acetate, and α-terpinyl acetate (R=acetyl). Some non-limiting examples of synthetic lactone fragrances include coumarin, jasmine lactone, muskalactone, and peach aldehyde. Some non-limiting examples of synthetic ether fragrances include ambroxan, anther, and galaxolide. Some non-limiting examples of synthetic nitrile fragrances include cinnamonitrile and gernonitrile. Finally, some non-limiting examples of synthetic polyfunctional fragrances include amyl salicylate, isoeugenol, hedione, heliotropine, lyral, and vanillin.

The composition may include a mixture of fragrances including a mixture of natural and synthetic fragrances. The fragrance can be present in a composition in an amount up to about 5 wt. %, preferably from 0 to about 3 wt. %, from about 0 to about 1 wt. %, and from about 0 to about 0.2 wt. %.

Dye

The composition may optionally include a dye. Examples of dyes include any water soluble or product soluble dye, any FD&C or D&C approved dye.

Methods of Making the Compositions

The compositions of to the invention are easily produced by any of a number of known art techniques. Conveniently, a part of the water is supplied to a suitable mixing vessel further provided with a stirrer or agitator, and while stirring, the remaining constituents are added to the mixing vessel, including any final amount of water needed to provide to 100% wt. of the inventive composition.

The compositions may be packaged in any suitable container particularly flasks or bottles, including squeeze-type or pump bottles, as well as bottles provided with a spray apparatus (e.g. trigger spray) which is used to dispense the composition by spraying. The selected packaging may have a pump head foamer. Examples of commercially available pump head foamers include the F2 foamer from Rexam PLC (London, England, formerly Airspray), and the RF-17 Palm Foamer from Rieke Corporation (Auburn, Indiana). Accordingly the compositions are desirably provided as concentrates or ready to use products in a manual or automated dispensing equipment.

The composition may be provided in various packaging sizes. Examples of packaging sizes include 1.5 oz, 500 ml and 1 liter bottles.

Whereas the compositions of the present invention are intended to be used in the types of liquid forms described, nothing in this specification shall be understood as to limit the use of the composition according to the invention with a further amount of water to form a solution there from. Conversely, nothing in the specification shall be also understood to limit the forming of a "super-concentrated" composition based upon the composition described above Such a super-concentrated ingredient composition is essentially the same as the compositions described above except in that they include a lesser amount of water.

Methods Employing the Compositions

The invention includes compositions and methods for reducing the population of a microorganism on skin, a method for treating a disease of skin, and the like. These compositions and methods can operate by contacting the body with a composition of the invention. Contacting can include any of numerous methods for applying a composition of the invention, such as spraying the compositions, immersing, foam or gel treating the skin with the composition, or a combination thereof. The compositions and methods may be used without further dilution with water or other suitable diluents or may be supplied as concentrated compositions. The concentrated compositions may be diluted prior to packaging or diluted prior to/at the point of use The concentrated compositions may be diluted at a concentrate: diluent ratio from about 1:1 to about 1:10. More preferably, the concentrated compositions may be diluted at a concentrate:diluent ration from about 1:3 to about 1:8. The concentrated compositions may be diluted manually or through automated dispensing and/or diluting equipment.

The compositions of the invention may be combined with treated or untreated water. For example, the compositions may be combined with aerated, chlorinated, desalinated, disinfected, reverse osmosis (RO) and/or filtered water. The compositions may also be combined with water sources containing mineral ions such as, but not limited to calcium, magnesium, iron, copper, manganese, bicarbonate, phosphate, silicate, sulfate, fluoride, chloride, bromide, hydroxide, nitrate, nitrite and the like. Additionally the concentrate compositions may be diluted at or prior to the point of use with water pretreated with coagulant and/or flocculants.

The compositions of the invention can be included in any skin application products such, sanitizers, deodorizers, antiseptics, fungicides, germicides, virucides, waterless hand sanitizers, and pre- or post-surgical scrubs, preoperative skin preps.

Embodiments of the Present Invention

The antimicrobial composition of the present invention has a high broad spectrum of antimicrobial efficacy, high foam and reduced irritation to mammalian tissue. Exemplary compositions are provided in the following tables.

TABLE A

Antimicrobial Composition with improved Foam Stability
(Expressed as Weight Percentage)
Antimicrobial composition (pH 5.0-6.7)

| Ingredient | Example | Preferred Embodiment (% w/w) | | More Preferred Embodiment (% w/w) | |
|---|---|---|---|---|---|
| | | Lower Limit | Upper Limit | Lower Limit | Upper Limit |
| Cationic Active Ingredient | Quaternary Ammonium Compound (QAC) [Alkyl Dimethyl Benzyl Ammonium Chloride (ADBAC)] | 0.4 | 1.5 | 0.5 | 1.0 |
| Quaternized Sugar-Derived Surfactant | Quaternary functionalized alkyl polyglucoside or Polyquaternary functionalized alkyl polyglucoside | 0.1 | 4.5 | 0.25 | 2.5 |
| Foam Boosting Surfactant | Dimethyl amine oxide; alkyl polyglucoside | 0.1 | 12.0 | 1.0 | 5.0 |
| Adjuvants (Dermal) | Glycerin, Sorbitol, Esters, Polyquats, Glycols, | 1.0 | 30.0 | 5.0 | 25.0 |
| Foam Stabilizing Polymer | DADMAC/ acrylamide | 0.05 | 18.0 | 0.1 | 10 |
| Foam Solubilizer | Hexylene glycol | 0.1 | 10.0 | 0.5 | 8 |
| Chelating agent | EDTA | 0.1 | 10.0 | 0.5 | 8 |

Antimicrobial Dermal Cleanser

TABLE 2

Antimicrobial Dermal Wash Exemplary Composition
(Expressed as Weight Ratio)
Antimicrobial Dermal Wash (pH 5.0-6.7)

| | | Preferred Embodiment (Weight Ratio) | | Most Preferred Embodiment (Weight Ratio) | |
|---|---|---|---|---|---|
| Ingredient | Example | Lower Limit | Upper Limit | Lower Limit | Upper Limit |
| Cationic Active Ingredient | Quaternary Ammonium Compound (QAC) [Alkyl Dimethyl Benzyl Ammonium Chloride (ADBAC)] | 1.0 | 1.0 | 1.0 | 1.0 |
| Quaternized Sugar-Derived Surfactant | Quaternary functionalized alkyl polyglucoside or Polyquaternary functionalized alkyl polyglucoside | 0.25 | 3.0 | 0.5 | 2.5 |
| Foam Boosting Surfactant | Dimethyl amine oxide; alkyl polyglucoside | 0.25 | 8.0 | 2.0 | 5.0 |
| Adjuvants (Dermal) | Glycerin, Sorbitol, Esters, Polyquats, Preservative | 2.5 | 16.0 | 4.0 | 10.0 |

TABLE 3

Dermal Cleanser Exemplary Composition
(Expressed as Weight Percentage)
Dermal Cleanser (pH 5.5-7.5)

| | | Preferred Embodiment (% w/w) | | Most Preferred Embodiment (% w/w) | |
|---|---|---|---|---|---|
| Ingredient | Example | Lower Limit | Upper Limit | Lower Limit | Upper Limit |
| Cationic Active Ingredient | Quaternary Ammonium Compound (QAC) [Alkyl Dimethyl Benzyl Ammonium Chloride (ADBAC)] | 0.3 | 5.0 | 0.5 | 4.0 |
| Quaternized Sugar-Derived Surfactant | Quaternary functionalized alkyl polyglucoside or Polyquaternary functionalized alkyl polyglucoside | 0.1 | 15.0 | 0.25 | 10.0 |
| Foam Boosting Surfactant | Dimethyl amine oxide; alkyl polyglucoside | 0.1 | 40.0 | 2.0 | 20.0 |
| Adjuvants (Dermal) | Glycerin, Sorbitol, Esters, Polyquats, Preservative | 1.0 | 25.0 | 1.75 | 15.0 |

TABLE 4

Dermal Cleanser Exemplary Composition
(Expressed as Weight Ratio)
Dermal Cleanser (pH 5.5-7.5)

| | | Preferred Embodiment (% w/w) | | Most Preferred Embodiment (% w/w) | |
|---|---|---|---|---|---|
| Ingredient | Example | Lower Limit | Upper Limit | Lower Limit | Upper Limit |
| Cationic Active Ingredient | Quaternary Ammonium Compound (QAC) [Alkyl Dimethyl Benzyl Ammonium Chloride (ADBAC)] | 1.0 | 1.0 | 1.0 | 1.0 |
| Quaternized Sugar-Derived Surfactant | Quaternary functionalized alkyl polyglucoside or Polyquaternary functionalized alkyl polyglucoside | 0.3 | 3.0 | 0.5 | 2.5 |
| Foam Boosting Surfactant | Dimethyl amine oxide; alkyl polyglucoside | 0.3 | 8.0 | 1.0 | 5.0 |
| Adjuvants (Dermal) | Glycerin, Sorbitol, Esters, Polyquats, Preservative | 3.3 | 5.0 | 3.5 | 3.75 |

TABLE 5

Surgical Scrub Exemplary Composition
(Expressed as Weight Percentage)
Surgical Scrub (pH 5.5-7.5)

| | | Preferred Embodiment (% w/w) | | Most Preferred Embodiment (% w/w) | |
|---|---|---|---|---|---|
| Ingredient | Example | Lower Limit | Upper Limit | Lower Limit | Upper Limit |
| Cationic Active Ingredient | Chlorhexidine Gluconate (CHG) | 1 | 6.0 | 1.5 | 5.0 |

TABLE 5-continued

Surgical Scrub Exemplary Composition
(Expressed as Weight Percentage)
Surgical Scrub (pH 5.5-7.5)

| Ingredient | Example | Preferred Embodiment (% w/w) | | Most Preferred Embodiment (% w/w) | |
|---|---|---|---|---|---|
| | | Lower Limit | Upper Limit | Lower Limit | Upper Limit |
| Quaternized Sugar-Derived Surfactant | Quaternary functionalized alkyl polyglucoside or Polyquaternary functionalized alkyl polyglucoside | 0.2 | 18.0 | 0.6 | 12.5 |
| Foam Boosting Surfactant | Dimethyl amine oxide; alkyl polyglucoside | 0.2 | 36.0 | 1.5 | 25.0 |
| Adjuvants (Dermal) | Glycerin, Sorbitol, Esters, Polyquats, Preservative | 1.0 | 25.0 | 2.0 | 10.0 |

TABLE 6

Surgical Scrub Exemplary Composition (Expressed as Weight Ratio)
Surgical Scrub (pH 5.5-7.5)

| Ingredient | Example | Preferred Embodiment (% w/w) | | Most Preferred Embodiment (% w/w) | |
|---|---|---|---|---|---|
| | | Lower Limit | Upper Limit | Lower Limit | Upper Limit |
| Cationic Active Ingredient | Chlorhexidine Gluconate (CHG) | 1.0 | 1.0 | 1.0 | 1.0 |
| Quaternized Sugar-Derived Surfactant | Quaternary functionalized alkyl polyglucoside or Polyquaternary functionalized alkyl polyglucoside | 0.2 | 3.0 | 0.4 | 2.5 |
| Foam Boosting Surfactant | Dimethyl amine oxide; alkyl polyglucoside | 0.2 | 6.0 | 1.0 | 5.0 |
| Adjuvants (Dermal) | Glycerin, Sorbitol, Esters, Polyquats, Preservative | 1.0 | 4.2 | 1.3 | 2.0 |

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

Materials used in the described embodiments include, but are not limited to: Stearyldimonium-hydroxypropyl Laurylglucosides Chloride, Cocoglucosides Hydroxypropyl-trimonium Chloride, Laurylglucosides Hydroxypropyl-trimonium Chloride, Poly (Lauryldimonium-hydroxypropyl Decylglucosides Chloride), Poly (Stearyldimonium-hydroxypropyl Decylglucosides Chloride), Poly (Stearyldimonium-hydroxypropyl Laruylglucosides Chloride), Poly (Trimonium-hydroxypropyl Cocoglucosides Chloride).

The following methods were used in the preparation and testing of the examples:

Antimicrobial and Microbial Efficacy:

(a) Determination of Time Kill Activity: The activity of antimicrobial compositions was measured by the time kill method [ASTM E 2315 *Standard Guide for Assessment of Antimicrobial Activity Using a Time Kill Procedure*], whereby the survival of challenged organisms exposed to an antimicrobial test composition is deterred as a function of time. In this test, a diluted aliquot of the composition is brought into contact with a known population of test bacteria for a specified time period at a specified temperature. The test composition is neutralized at the end of the time period, which arrests the antimicrobial activity of the composition. The percent or, alternatively, log reduction from the original bacteria population is calculated. In general, the time kill method is known to those skilled in the art. In addition, comparative data on the foam profile of representative systems is shown.

(b) The composition can be tested at any concentration from 0-100%. The choice of which concentration to use is at the discretion of the investigator, and suitable concentrations are readily determined by those skilled in the art. All testing if performed in triplicate, the results are combined, and the average log reduction is reported.

(c) The choice of contact time period also is at the discretion of the investigator. Any contact time period can be chosen. Typical contact times range from 15 second to 5 minutes, with 30 seconds and 1 minute being typical contact times. The contact temperature also can be any temperature, typically room temperature, or about 25 degrees Celsius.

(d) The microbial suspension, or test inoculum, is prepared by growing a microbial culture on any appropriate solid media (e.g., agar). The microbial population then is washed from the agar with sterile physiological saline and the population of the microbial suspension is adjusted to about $10^8$ colony forming units per ml (cfu/ml).

(e) The table below lists the test microbial cultures used in the following tests and includes the name of the bacteria, the ATCC (American Type Culture Collection) identification number, and the abbreviation for the name of the organism used hereafter.

| Organism Name | ATCC # | Abbreviation |
|---|---|---|
| S. aureusylococcus | 6538 | S. aureus |
| Escherichia coli | 112229 | E. coli |

*S. aureus* is a Gram positive bacteria, whereas, *E. coli* is a Gram negative bacteria.

The log reduction is calculated using the formula:

$$\text{Log reduction} = \log_{10}(\text{numbers control}) - \log_{10}(\text{test sample survivors}).$$

Foam Height Determination

The foam height was determined with the following procedural steps:
1. Prepare a 1% solution of the product in 5 grain water.
2. Pour 150 mL of the solution into a blender
3. Mix on medium speed 10 seconds.
4. Pour into a 1000 mL beaker and measure foam height.
5. Measure foam height at 3 and 5 minutes.

Foam Stability Determination

The foam stability was determined by using the difference between the foam/air interference and the foam/aqueous interface 5 minutes after pouring a 1% solution into a 1000 mL beaker.

In Vitro Irritancy Determination

In vitro irritancy was assessed by an external testing facility using Matek Corporation's "EpiDerm MTT ET-50 Protocol (EPI-200)".

The test consists of a topical exposure of the neat test chemical to a reconstructed human epidermis (RhE) model followed by a cell viability test. Cell viability is measured by dehydrogenase conversion of MTT [(3-4,5-dimethyl thiazole 2-yl) 2,5-diphenyltetrazolium bromide], present in cell mitochondria, into a blue formazan salt that is quantitatively measured after extraction from tissues. The reduction of the viability of tissues exposed to chemicals in comparison to negative controls (treated with water) is used to predict the skin irritation potential.

EpiDerm tissues are conditioned by incubation of release transport-stress related compounds and debris overnight. After pre-incubation, tissues are topically exposed to the test chemicals for 60 minutes. Preferably, three tissues are used per test chemical (TC) and for the positive control (PC) and negative control (NC). Tissues are then thoroughly rinsed, blotted to remove the test substances, and transferred to fresh medium. Tissues are incubated for 42 hrs. Afterwards, the MTT assay is performed by transferring the tissues to 24-well plates containing MTT medium (1 mg/mL) after a 3 hr MTT incubation, the blue formazan salt formed by cellular mitochondria is extracted with 2.0 mL/tissue of isopropanol and the optical density of the extracted formazan is determined using a spectrophotometer at 570 nm. Relative cell viability is calculated for each tissue as % of the mean of the negative control tissues. Skin irritation potential of the test material is predicted if the remaining relative cell viability is below 50%.

Foam Resistance Determination

The foam resistance was determined by measuring 65 grams of the test product into a blender and blending for about 10 seconds on medium speed. Thereafter, the test solution was poured into a cylinder and a plastic ball was dropped into the test solution and timed to determine how many seconds it took for the plastic ball to drop from a first pre-determined level to a second pre-determined level, e.g., from 100 mL mark on the cylinder to the 40 mL mark on the cylinder.

Example 1

The following Figures demonstrate efficacy data of the present antimicrobial composition, using various cationic active ingredients, quaternary sugar-derived surfactants and optional foam boosting surfactants.

Table 7 and FIG. 1 (Log Kill of Cationic Active Ingredients): The following figures illustrate the efficacy following a 30 second exposure time of three different cationic active ingredients, specifically, 0.5% Quat (Benzalkonium Chloride), 2% CHG (Chlorhexidine Gluconate), and 1% PHMB (polyhexamethylene biguanide) in a representative surfactant system.

Table 7 illustrates the formulas for the three cationic active ingredient systems tested. Both the quaternary sugar-derived surfactant and foam boosting surfactant were held constant and only the cationic active ingredient was changed between the three tests performed. The results are illustrated in FIG. 1.

TABLE 7

| Active Ingredient System | Ingredients | Level (% w/w) |
|---|---|---|
| Quaternary Ammonium Compound (Quat) | Active Ingredient | 0.5 |
| | Quaternized Sugar-Derived Surfactant | 1.25 |
| | Foam Boosting Agent | 1.95 |
| Chlorhexidine Gluconate (CHG) | Active Ingredient | 2.0 |
| | Quaternized Sugar-Derived Surfactant | 1.25 |
| | Foam Boosting Agent | 1.95 |
| Poly Hexamethylene Biguanide (PHMB) | Active Ingredient | 1.0 |
| | Quaternized Sugar-Derived Surfactant | 1.25 |
| | Foam Boosting Agent | 1.95 |

As illustrated in FIG. 1, all three cationic active ingredients had high cidal activity against *S. aureus* and *E. coli* bacteria within a 30 second exposure time.

Figure 2:
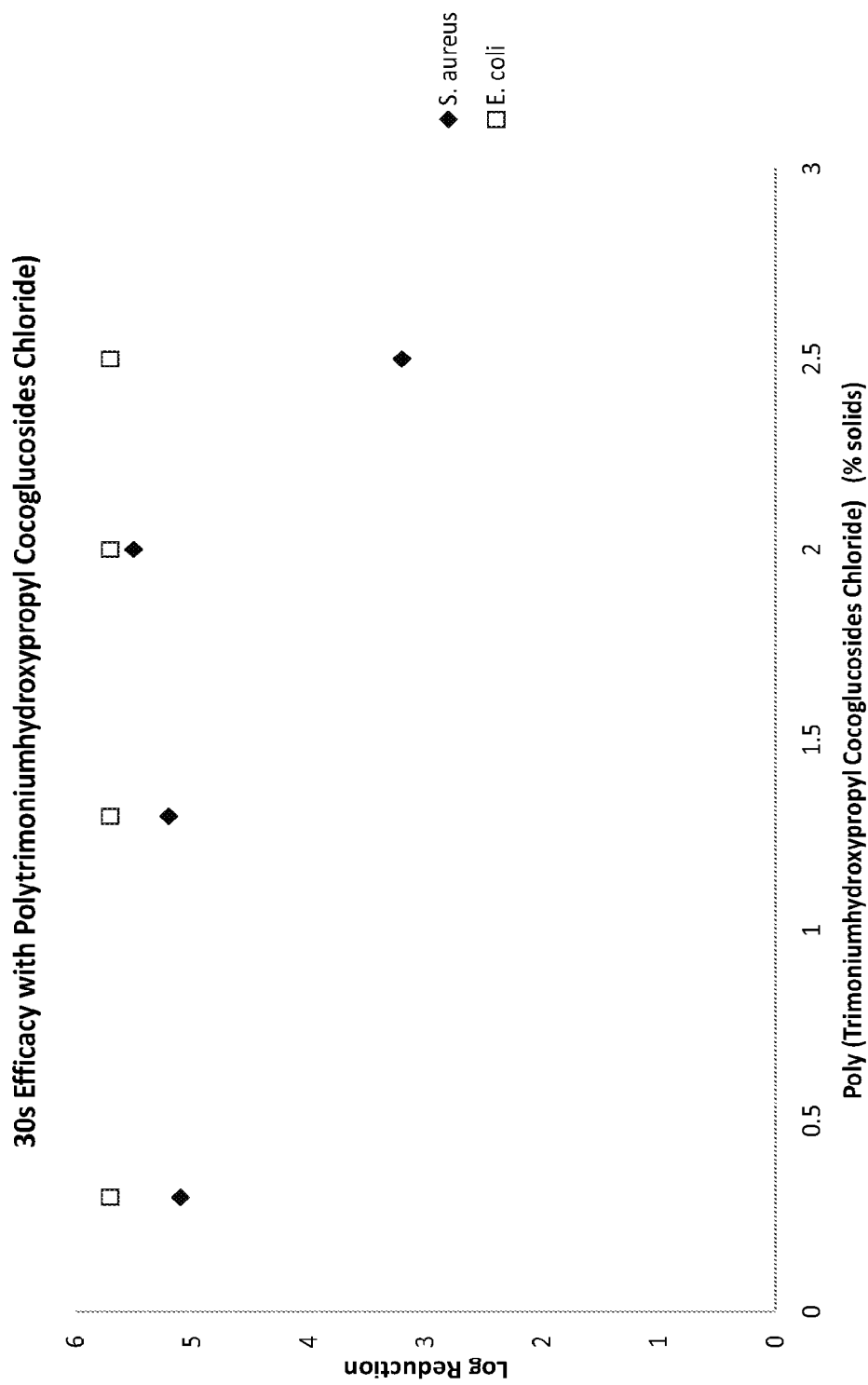
FIG. 2 illustrates a graph depicting the test results of the efficacy against *S. aureus* and *E. coli* bacteria with increased concentrations of quaternary sugar-derived surfactants, specifically, poly (trimoniumhydroxypropyl cocogluocosides) chloride). The amount and type of cationic active ingredient (0.5% ADBAC) and foam boosting surfactant (1.95% alkyl dimethyl amine oxide) was held constant.

Table 8 and FIG. 2 (Log Kill of Quaternary Sugar-Derived Surfactants): Next, Applicants tested the efficacy against *S. aureus* and *E. coli* bacteria with increased concentrations of quaternary sugar-derived surfactants, specifically, Poly (Trimoniumhydroxypropyl Cocogluocosides Chloride). The amount and type of cationic active ingredient (0.5% ADBAC Quat) and foam boosting surfactant (1.95% Alkyl Dimethyl Amine Oxide) was held constant. Table 8 below illustrates the quantitative results of this test and FIG. 2 illustrates the graphical results.

TABLE 8

| Quaternized Sugar-Derived Surfactant (% w/w) | Active Ingredient (% w/w) | Foam Boosting Agent (% w/w) | S. aureus Log Reduction | E. coli Log Reduction |
|---|---|---|---|---|
| 0.3 | 0.5 | 1.95 | >5.0 | >5.0 |
| 1.3 | 0.5 | 1.95 | >5.0 | >5.0 |
| 2.5 | 0.5 | 1.95 | 3.2 | >5.0 |

As Table 8 and FIG. 2 illustrate, the quaternary sugar-derived surfactant has a high cidal activity against *S. aureus* and *E. coli* bacteria after only 30 seconds of exposure. Also, the tolerance of the quaternary sugar derived surfactant against bacteria is shown. Furthermore, it is clearly illustrated that an increased concentration of quaternary sugar-derived surfactant maintains a good log kill of bacteria up until a 1 to 4 ratio of quaternary sugar-derived surfactant to cationic active ingredients.

Figure 3:
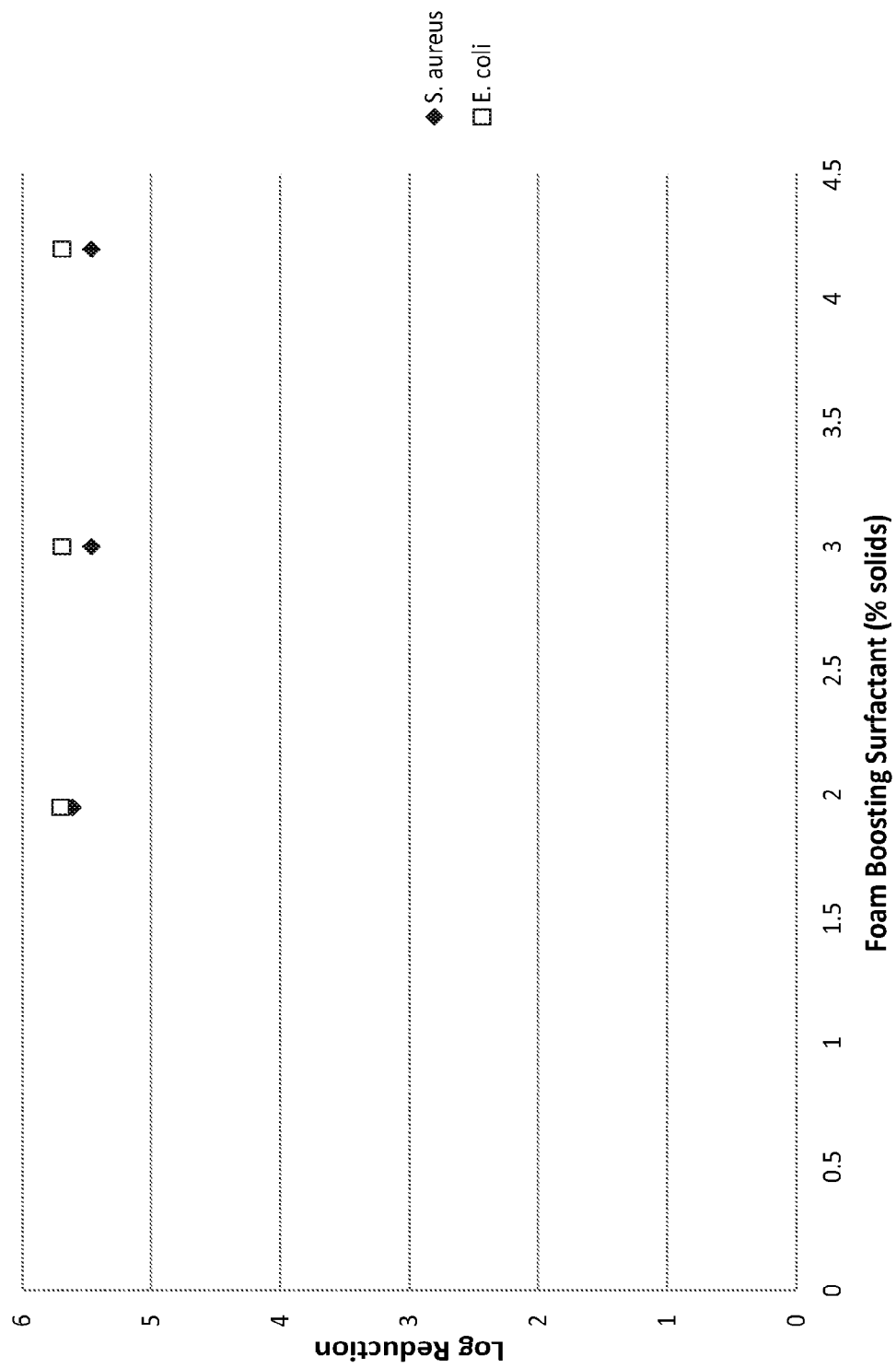
FIG. 3 illustrates a graph depicting the test results of the efficacy with increased concentrations of foam boosting surfactants, specifically, amine oxide. The amount and type of cationic active ingredient (0.5% ADBAC) and quaternary sugar-derived surfactant (1.25% poly trimoniumhydroxypropyl cocoglucosides chloride) were held constant.

Table 9 and FIG. 3 (Log Kill of Foam Boosting Surfactants): Table 15 and FIG. 3 illustrate the efficacy with increased concentrations of foam boosting surfactants, specifically, amine oxide. The amount and type of cationic active ingredient (0.5% ADBAC Quat) and Quaternary sugar-derived surfactant (1.25% Poly Trimoniumhydroxypropyl Cocoglucosides Chloride) were held constant. Table 9 below illustrates the quantitative results of this test and FIG. 3 illustrates the graphical results.

TABLE 9

| Foam Boosting Agent (% w/w) | Active (% w/w) | Quaternized Sugar-Derived Surfactant (% w/w) | S. aureus Log Reduction | E. coli Log Reduction |
| --- | --- | --- | --- | --- |
| 1.95 | 0.5 | 1.25 | >5.5 | >5.5 |
| 3.0 | 0.5 | 1.25 | >5.5 | >5.5 |
| 4.2 | 0.5 | 1.25 | >5.5 | >5.5 |

As Table 9 and FIG. 3 illustrate, the foam boosting surfactant has a high cidal activity against *S. aureus* and *E. coli* bacteria after only 30 seconds of exposure. Also, the tolerance of the foam boosting surfactant against bacteria is shown. Furthermore, it is clearly illustrated that a broad range of foam boosting surfactant maintains a good log kill of bacteria.

Figure 4:
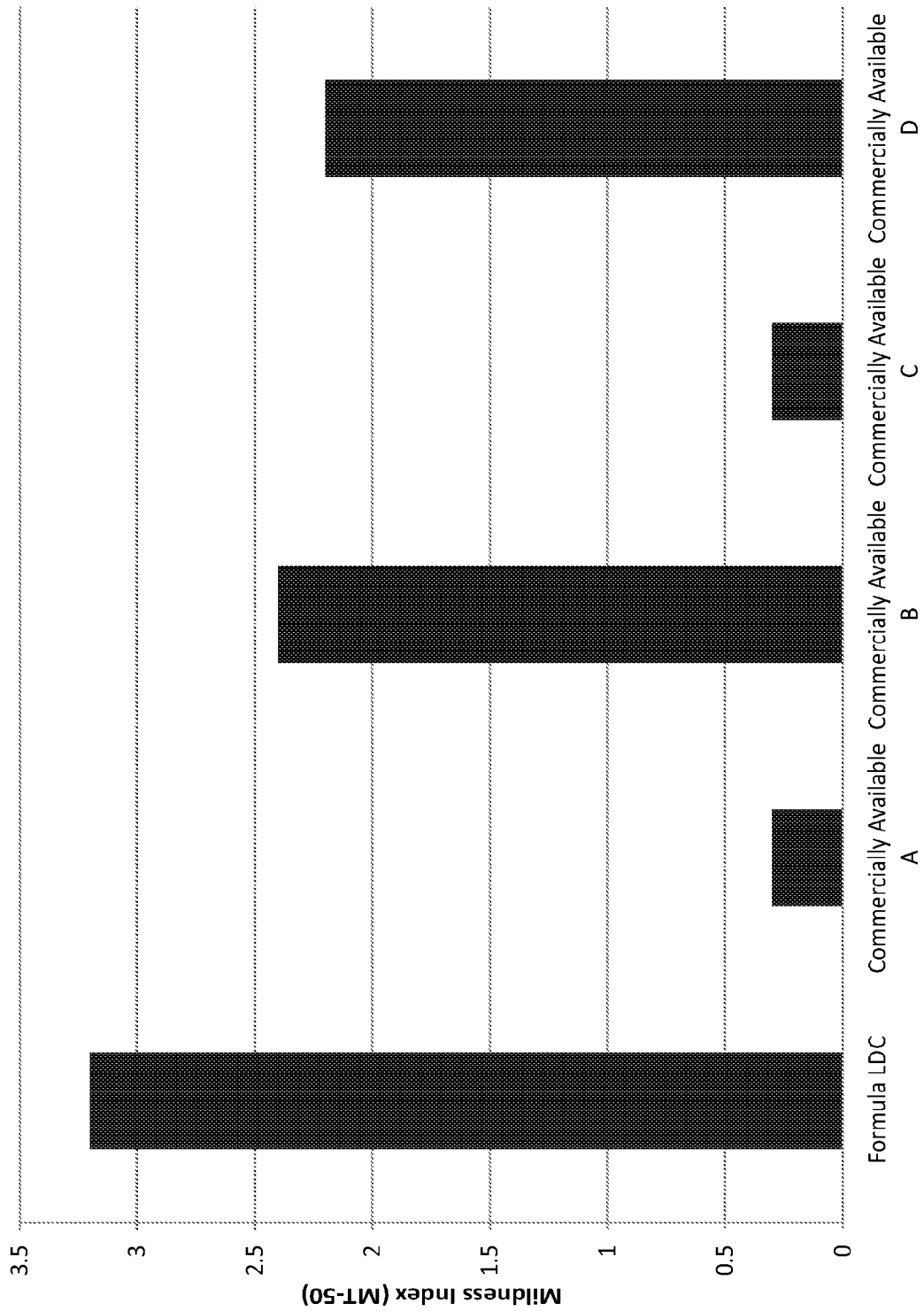
FIG. 4 illustrates the dermal irritancy (mildness) of the preferred embodiment for an antimicrobial dermal cleanser to four commercially available antimicrobial soaps.

FIG. 4 (Mildness Index for an Antimicrobial Dermal Cleanser Embodiment): Applicants tested the dermal irritancy (mildness) of the preferred embodiment for an antimicrobial Dermal Cleanser as illustrated in Table 12 to four commercially available antimicrobial soaps. Commercially Available Products A, C and D are available by Gojo Medicated, Akron, Ohio and Commercially Available Product B is available by Dial a subsidiary of Henkel Corporation, Dusseldorf, Germany. As illustrated in FIG. 4, the antimicrobial dermal cleanser of the current invention has a high relative mildness index especially in comparison to antimicrobial hand soaps that are commercially available.

Figure 5:
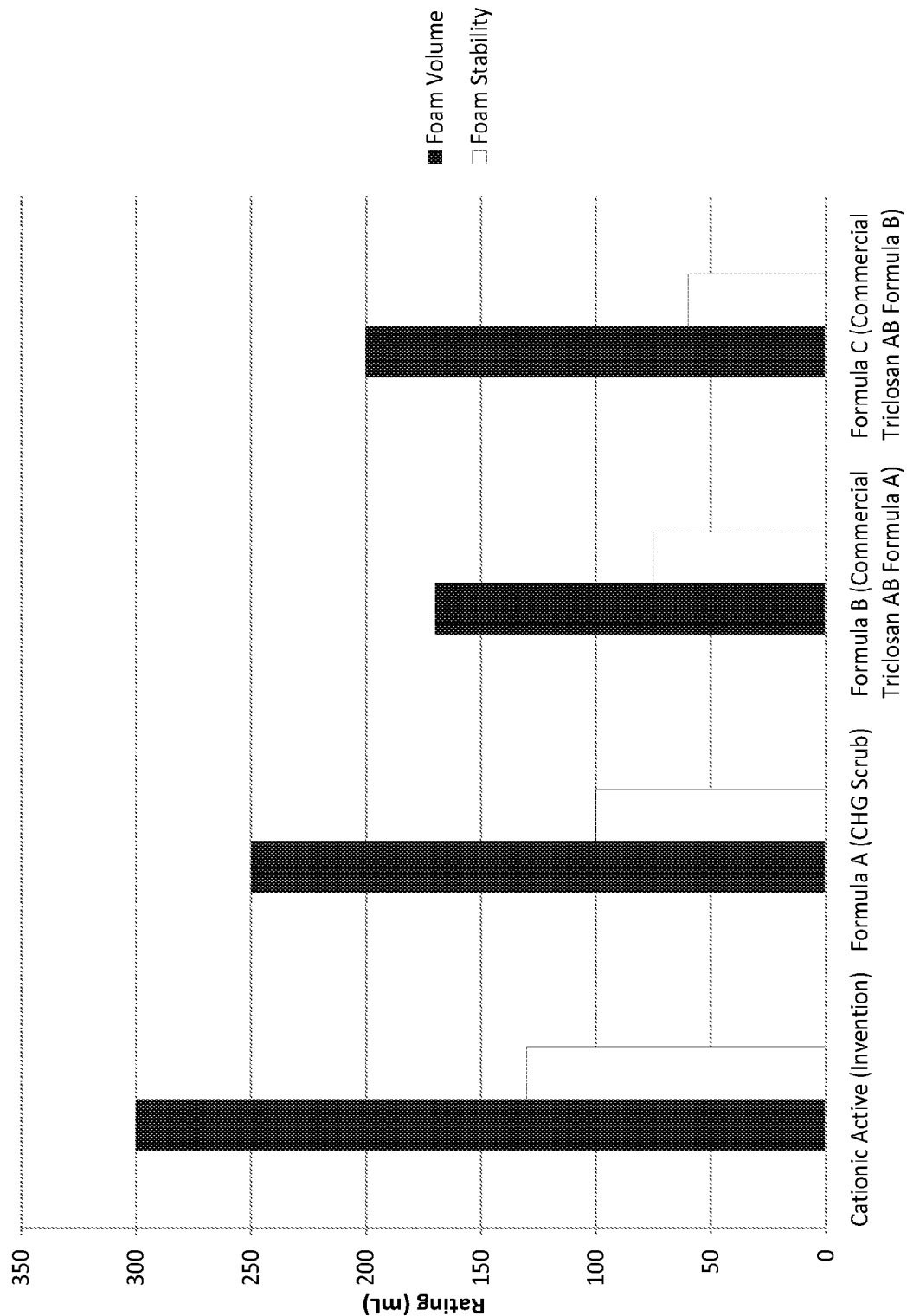
FIG. 5 illustrates the foam profile of the preferred embodiment for an antimicrobial dermal cleanser to three commercially available antimicrobial soaps.
Figure 6:
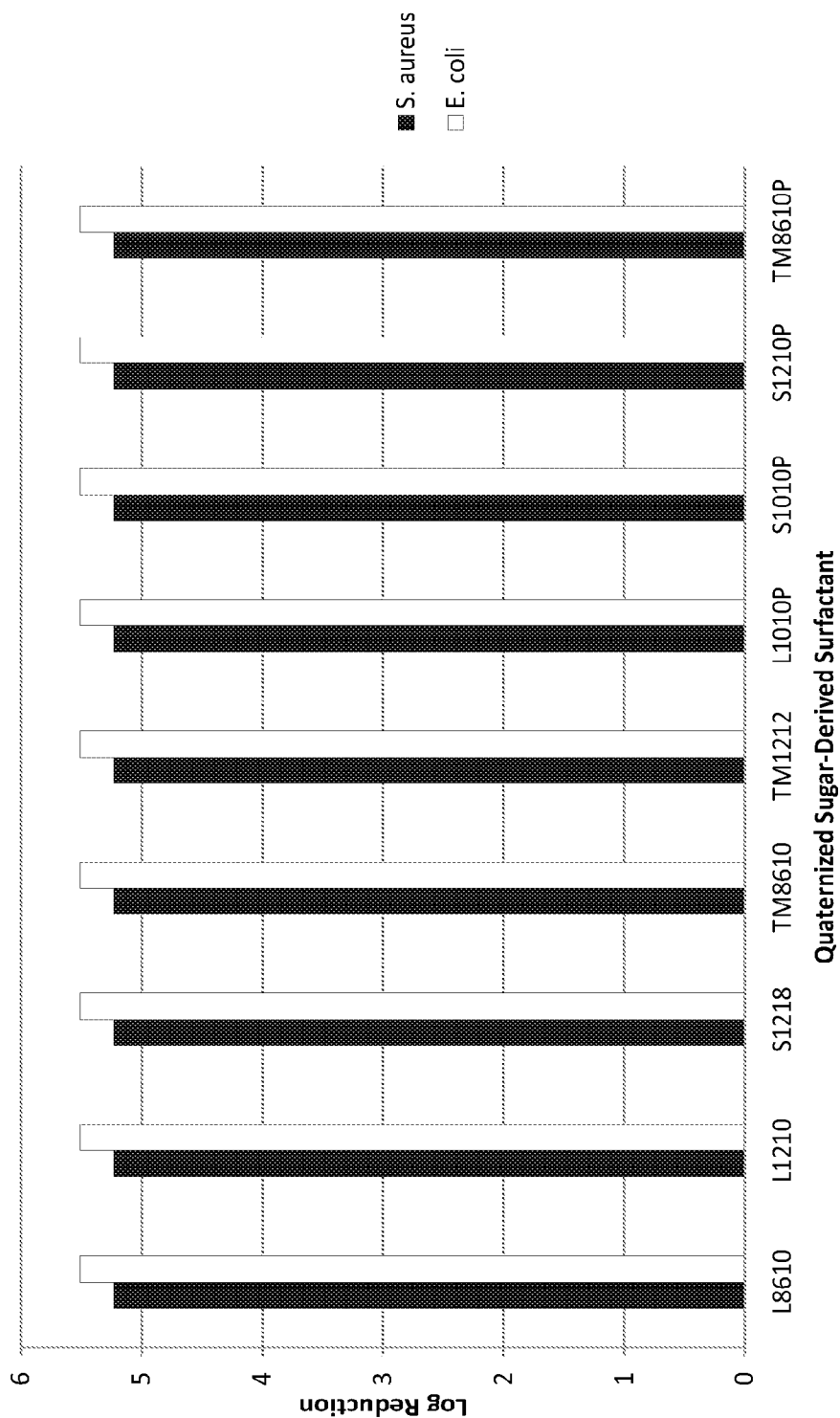
FIG. 6 illustrates the efficacy against *S. aureus* and *E. coli* bacteria following a 30 second exposure to a cationic active in combination with quaternary sugar-derived surfactants, held constant at 1.25% and an n-alkyl ($C_{12-16}$) dimethylamine oxide foam boosting surfactant.

FIG. 5 (Foam Profile for an Antimicrobial Dermal Cleanser Embodiment): Applicants tested the foam profile of the preferred embodiment for an antimicrobial Dermal Cleanser as illustrated in Table 12 to three commercially available antimicrobial soaps. As illustrated in FIG. 6, the antimicrobial dermal cleanser of the current invention has both good foam volume and foam stability especially in comparison to antimicrobial hand soaps that are commercially available.

Table 10 and FIG. 6 (Efficacy of Cationic Actives in Combination with Quaternary Sugar Derived Surfactants and Alkyl Dimethyl Amine Oxide): Applicants tested the efficacy against *S. aureus* and *E. coli* bacteria with various quaternary sugar-derived surfactants, held constant at 1.25%. The amount and type of cationic active ingredient (0.5% ADBAC Quat) and foam boosting surfactant (1.95% Alkyl Dimethyl Amine Oxide) was held constant.

TABLE 10

| Quaternized Sugar-Derived Surfactant (1.25 % w/w) | Active Ingredient (% w/w) | Foam Boosting Surfactant (% w/w) | S. aureus Log Reduction | E. coli Log Reduction |
| --- | --- | --- | --- | --- |
| (L8610) Lauridimonium-hydroxypropyl Cocoglucosides Chloride | 0.5 | 1.95 | >5.0 | >5.0 |
| (L1210) Lauridimonium-hydroxypropyl Laurylglucosides Chloride | 0.5 | 1.95 | >5.0 | >5.0 |
| (S1218) Stearyldimonium hydroxypropyl Laurylglucosides Chloride | 0.5 | 1.95 | >5.0 | >5.0 |
| (TM8610) Cocoglucosides Hydroxypropyl-trimonium Chloride | 0.5 | 1.95 | >5.0 | >5.0 |
| (TM1212) Laurylglucosides Hydroxypropyl-trimonium Chloride | 0.5 | 1.95 | >5.0 | >5.0 |
| (L1010P) Poly (Lauryldimonium-hydroxypropyl Decylglucosides Chloride) | 0.5 | 1.95 | >5.0 | >5.0 |
| (S1010P) Poly (Stearyldimonium-hydroxypropyl Decylglucosides Chloride) | 0.5 | 1.95 | >5.0 | >5.0 |
| (S1210P) Poly (Stearyldimonium hydroxypropyl Laruylglucosides Chloride) | 0.5 | 1.95 | >5.0 | >5.0 |
| (TM8610P) Poly (Trimoniumhydroxy-propyl Cocoglucosides Chloride) | 0.5 | 1.95 | >5.0 | >5.0 |

As Table 10 illustrates, a high log kill is maintained against *S. aureus* and *E. coli* bacteria for both quaternized sugar-derived surfactants and polyquaternized sugar-derived surfactants. The chain length of the sugar quaternary surfactant may be altered and yet still maintain high efficacy. The graphical results of the test are illustrated in FIG. 6.

Figure 7:
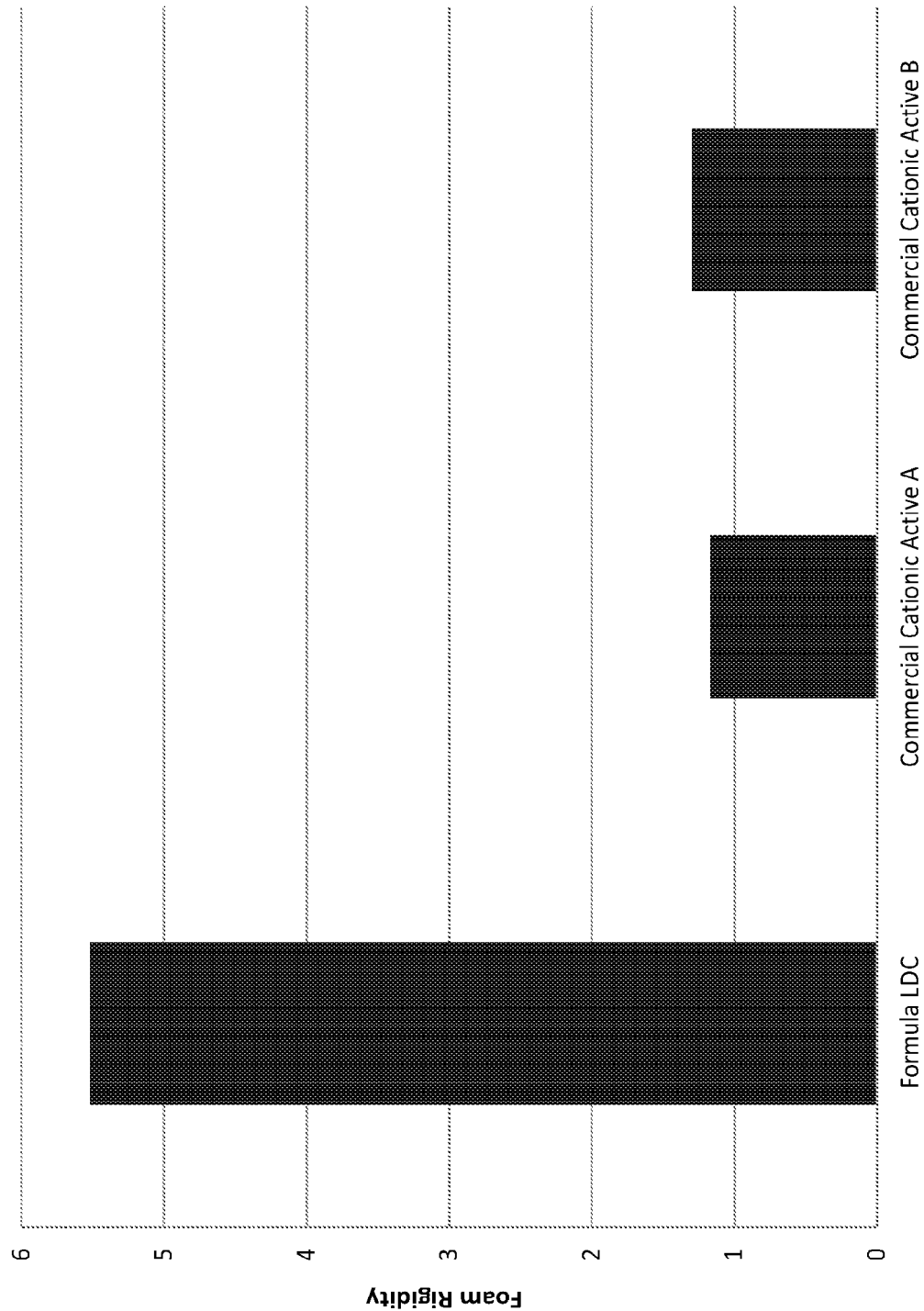
FIG. 7 illustrates the foam rigidity of the preferred embodiment for an antimicrobial dermal cleanser to two commercially available antimicrobial soaps with cationic actives.

Table 11 and FIG. 7 (Comparative Foam Rigidityl: Applicants tested the foam rigidity of an embodiment of the current invention for use in dermal applications as shown below in Table 11 in comparison to two commercially available products, Commercial Products E and F. Commercial Products E and F are traditional anionic surfactant base dermal washes containing a cationic active. Commercial Product E is commercially available by Proctor & Gamble, Cincinnati, Ohio and Commercial Product F is commercially available by Deb Group Limited, United Kingdom, England. The results of the foam rigidity test are illustrated in FIG. 7. As illustrated in FIG. 7, the foam rigidity of the dermal wash of the current invention is greater than commercially available cationic active dermal washes with a traditional anionic surfactant base.

Foam Rigidity Formula of Current Invention (pH of 5.5-7.5):

TABLE 11

| Component | Weight Percent |
| --- | --- |
| Water | 91.7 |
| Cationic Active (Quaternary Ammonium Compound) | 0.5 |
| Quaternized Sugar-Derived Surfactant | 0.7 |
| Foam Boosting Surfactant | 4.1 |
| Dermal Adjuvants | 3.0 |

Table 12 (Antimicrobial Efficacy of a Dermal Cleanser of the Current Invention): Applicants tested the efficacy of the dermal cleanser of the current invention by determining the log reduction of both gram positive and gram negative bacterial after 30 seconds of exposure.

Dermal Cleanser of Current Invention (pH of 5.5-7.5):

TABLE 12

| Component | Weight Percent Range |
|---|---|
| Water | 7.5-99.3 |
| Cationic Active (Quaternary Ammonium Compound) | 0.3-5 |
| Quaternized Sugar-Derived Surfactant | 0.05-7.5 |
| Foam Boosting Surfactant | 0.2-5 |
| Dermal Adjuvants | 0.1-7 |

Table 13 (Antimicrobial Efficacy of a Surgical Scrub of the Current Invention): Applicants tested the efficacy of the surgical scrub of the current invention by determining the log reduction of both gram positive and gram negative bacterial after 30 seconds of exposure.

Surgical Scrub of Current Invention (pH of 5.5-7.5):

TABLE 13

| Component | Weight Percent Range |
|---|---|
| Water | 56-97.8 |
| Cationic Active (Quaternary Ammonium Compound) | 1-6 |
| Quaternized Sugar-Derived Surfactant | 0.2-8 |
| Foam Boosting Surfactant | 0.5-10 |
| Dermal Adjuvants | 0.5-20 |

Example 2

Mackernium 007S—DADMAC/Acrylamide Copolymer (Rhodia)

Uniquat QAC50—Benzalkonium Chloride (Lonza)

Dissolvine 100S—Ethylenediamine Tetraacetic acid sodium salt (Akzo Nobel)

Barlox 12—N-Alkyl (C12-16) dimethyl amine oxide (Lonza)

Cola Lipid C—Cocamidopropyl PG dimonium chlorophosphate (Colonial Chemical)

PolySugaQuat TM8610P—Polyquaternium 77 (Colonial Chemical)

Glucam E20—Methyl Gluceth 20 (Lubrizol)

Cetiol HE—PEG-7 Glyceryl Cocoate (Cognis)

Ritasol SP 1005—PEG-12 Dimethicone (Rita Corporation)

Hest G-18-O—Glycereth-18 Ethylhexanoate (Global Seven)

Kathon CG—Methyl Isothiazolinone (DOW Chemical)

TABLE 14

| | Example #1 | Example #2 |
|---|---|---|
| USP Water | 74.4 | 73.7 |
| Acrylamide/DADMAC Copolymer | 0.6 | 0.59 |
| Benzalkonium Chloride, 50% | 2.5 | 2.4 |
| Tetrasodium Ethylenediaminetetraacetic acid, 40% | 0 | 0.99 |
| Lauryl Dimethylamine Oxide, 30% | 21.8 | 21.6 |
| Lactic Acid | 0.69 | 0.69 |
| Total | 100 | 100 |

TABLE 15

| | Example #3 |
|---|---|
| USP Water | 56.91 |
| Acrylamide/DADMAC Copolymer | 0.48 |
| Benzalkonium Chloride, 50% | 1.98 |
| Tetrasodium Ethylenediaminetetraacetic acid, 40% | 0.80 |
| Lauryl Dimethylamine Oxide, 30% | 17.58 |
| Polyquaterium 77 | 3.42 |
| Hexylene Glycol | 3.00 |
| Other functional components, fragrance, dermal adjuvants, pH adjuster, preservative | 15.83 |
| Total | 100 |

All samples were prepared using a 20% solution of examples 1-5 (tables 14-16) diluted in deionized water or 10 grain hardness water as indicated. The samples were then adjusted to the appropriate pH using lactic acid.

Figure 8:
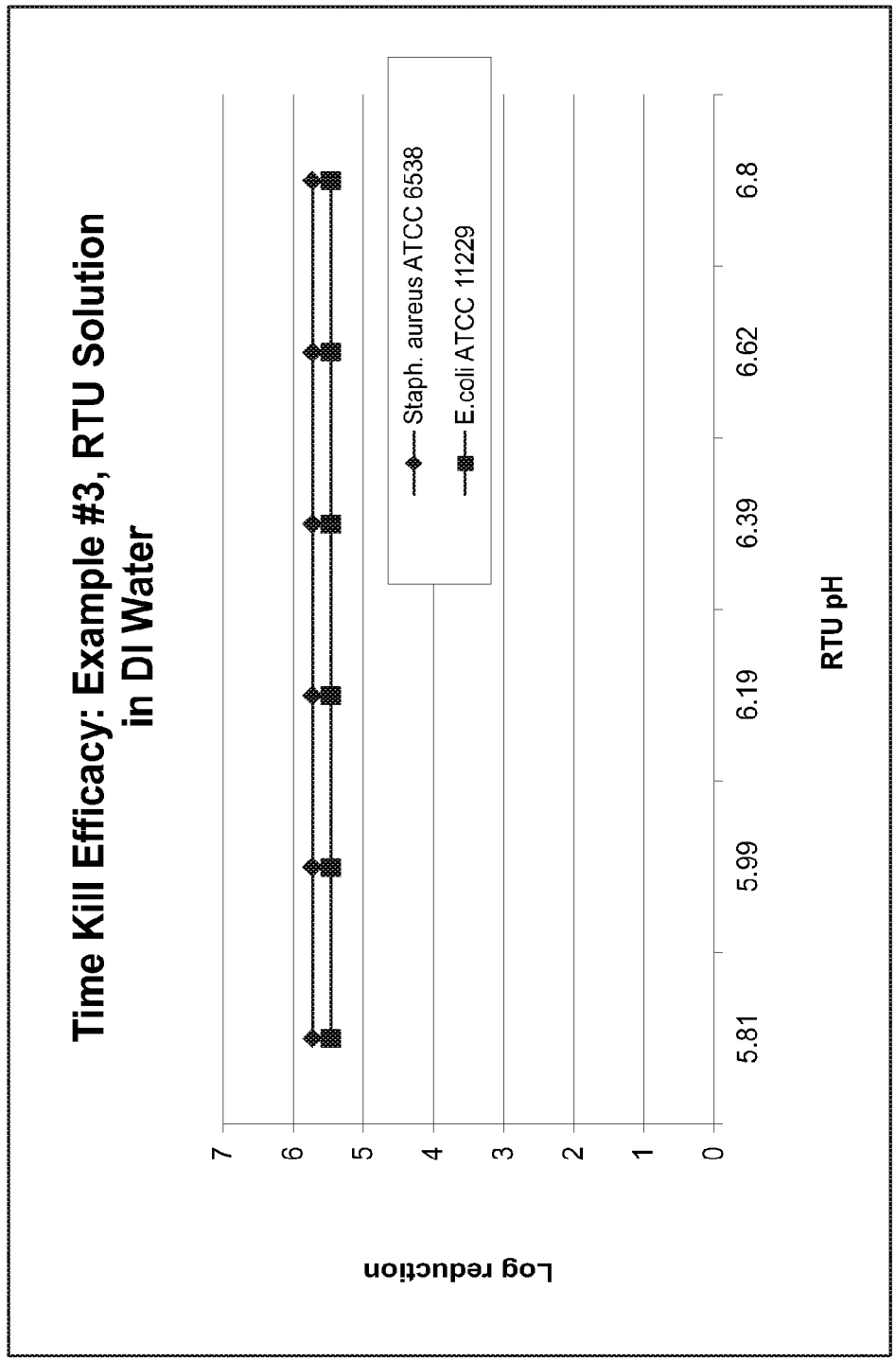
FIG. 8 is a graph showing the efficacy against *S. aureus* and *E. coli* bacteria over various pHs.

The results are shown in tables 16 and 17. The results of table 17 are depicted graphically in FIG. 8.

TABLES 16 AND 17

| | | Log Reduction | |
|---|---|---|---|
| Formulation | Water Hardness | Staph. Aureus ATCC 6538 | E. Coli ATCC 112229 |
| Example #1 | DI Water | >5.70 | >5.80 |
| Example #2 | DI Water | >5.70 | >5.80 |

| | | Exposure | | Log Reduction | |
|---|---|---|---|---|---|
| Formula | water | Time | RTU pH | Staph | E coli |
| Example #3 | DI | 30 sec | 5.81 | >5.72 | >5.46 |
| Example #3 | DI | 30 sec | 5.99 | >5.72 | >5.46 |
| Example #3 | DI | 30 sec | 6.19 | >5.72 | >5.46 |
| Example #3 | DI | 30 sec | 6.39 | >5.72 | >5.46 |
| Example #3 | DI | 30 sec | 6.62 | >5.72 | >5.46 |
| Example #3 | DI | 30 sec | 6.8 | >5.72 | >5.46 |

From table 16, one can see that the addition of chelating agent in example 2 allows for identical antimicrobial activity in hard water.

From table 17 one can see that the ready to use composition of the invention demonstrates stable antimicrobial activity across various pH differences.

Comparison of Chelating Agents Iminodisuccinic Acid (IDS) and Ethylenediamine Tetraacetic Acid (EDTA) at pH=6.4

The antimicrobial compositions of the invention where made with the same components with the exception of the two different chelating agents as indicated below in Table 18.

TABLE 18

| Raw Material | Example #4 | Example #5 |
|---|---|---|
| USP Water | 56.97 | 56.97 |
| Lauryl Dimethylamine Oxide 30% | 17.58 | 17.58 |
| Polyquaternium 7 (acrylamide/DADMAC copolymer) | 0.48 | 0.48 |
| Benzalkonium Chloride, 50% | 1.98 | 1.98 |
| Tetrasodium ethylenediaminetetraacetate, 40% | 0.00 | 1.00 |
| Sodium IDS, 34% | 1.17 | 0.00 |
| Polyquaternium 77 | 3.42 | 3.42 |

TABLE 18-continued

| Raw Material | Example #4 | Example #5 |
|---|---|---|
| Hexylene Glycol | 3.0 | 3.0 |
| Other functional components, fragrance, dermal adjuvants, pH adjuster | 15.4 | 15.57 |
| Total | 100.00 | 100.00 |

The results are shown in in Table 19.

TABLE 19

| | | Log Reduction | |
|---|---|---|---|
| Formulation | Water Hardness | Staph. Aureus ATCC 6538 | E. Coli ATCC 112229 |
| Example #4 | 10 grain | >4.90 | NDR* |
| Example #5 | 10 grain | >4.90 | >5.65 |

*No Detectable Reduction

The testing results indicate that antimicrobial efficacy is enhanced by chelating agents with high stability constants for $Ca^{2+}$ and $Mg^{2+}$.

Log Stability constant for IDS $Ca^{2+}$=5.2

Log Stability constants for EDTA $Ca^{2+}$=10.7

Additional Exemplary Formulations

| | Example 6 | Example 7 |
|---|---|---|
| USP Water | 74.4 | 73.7 |
| Acrylamide/DADMAC Copolymer | 0.6 | 0.59 |
| Benzethonium Chloride, 99.5% | 1.2 | 0 |
| Chlorhexidene Gluconate Powder, 99% | 0 | 1.2 |
| Tetrasodium Ethylenediaminetetraacetic acid, 40% | 0 | 0.99 |
| Lauryl Dimethylamine Oxide, 30% | 21.8 | 21.6 |
| Lactic Acid | 0.69 | 0.69 |
| Total | 100 | 100 |

| | Example 8 Wt % | Example 9 Wt % | Example 10 Wt % | Example 11 Wt % |
|---|---|---|---|---|
| USP Water | qs | qs | qs | qs |
| Acrylamide/DADMAC Copolymer | 0.3-0.5 | 0.3-0.5 | 0.3-0.5 | 0.3-0.5 |
| Benzethonium Chloride, 99% | 0.5 | 2 | 0 | 0 |
| Chlorhexidine Gluconate Salt, 20% | 0 | 0 | 2.5 | 10 |
| Tetrasodium Ethylenediaminetetraacetic acid, 40% | 0.5-1.0 | 0.5-1.0 | 0.5-1.0 | 0.5-1.0 |
| Lauryl Dimethylamine Oxide, 30% | 15-20 | 15-20 | 15-20 | 15-20 |
| Cocamidopropyl PG dimonium chlorophosphate, 50% | 4-7 | 4-7 | 4-7 | 4-7 |
| Polyquaterium 77 | 3-4 | 3-4 | 3-4 | 3-4 |
| Glycerine, 99.5% USP | 4-5 | 4-5 | 4-5 | 4-5 |
| Methyl Gluceth 20 | 1-2 | 1-2 | 1-2 | 1-2 |
| PEG-7 Glyceryl Cocoate | 1-2 | 1-2 | 1-2 | 1-2 |
| PEG-12 Dimethicone | 0.1-0.4 | 0.1-0.4 | 0.1-0.4 | 0.1-0.4 |
| Glycereth-18 Ethylhexanoate | 0.1-0.4 | 0.1-0.4 | 0.1-0.4 | 0.1-0.4 |
| RED #33 0.1% solution | 1 | 1 | 1 | 1 |
| Citrus Fragrance | qs | qs | qs | qs |
| Hexylene Glycol | 2-4 | 2-4 | 2-4 | 2-4 |
| Kathon CG | 0.1-0.2 | 0.1-0.2 | 0.1-0.2 | 0.1-0.2 |
| Lactic Acid | qs | qs | qs | qs |
| Total | 100 | 100 | 100 | 100 |

The above samples were made and tested in Examples 1 and 2.

The antimicrobial compositions of the present invention have several practical end uses, including hand cleansers, surgical scrubs, hand sanitizer gels, and similar personal care products. Additional types of compositions include foamed compositions, such as creams, mousses, and the like. The present antimicrobial compositions can be manufactured as dilute ready-to-use compositions, or as concentrates that are diluted prior to or at the point of use. The dilution may occur manually or via automated dispensing and/or diluting equipment.

Obviously, many modifications and variations of the invention as hereinbefore set forth can be made without departing from the spirit and scope thereof, and, therefore, only such limitations should be imposed as are indicated by the appended claims.

What is claimed:

1. A method of reducing bacterial, microbial, fungal or viral population on a dermal tissue of a mammal under hard water conditions comprising the step of:
    contacting the dermal tissue of a mammal with a dermal concentrate comprising
    (a) a cationic active ingredient, wherein the cationic active ingredient is an inorganic salt of an aromatic quaternary ammonium containing compound;
    (b) from about 0.1% to about 4.5% of a quaternized sugar-derived surfactant;
    (c) a foam boosting amine oxide surfactant;
    (d) from about 0.05 wt. % to about 18 wt. % of a foam boosting copolymer, wherein the foam boosting copolymer is a dimethyldiallylammonium chloride-acrylamide copolymer, wherein said dimethyldiallylammonium chloride-acrylamide copolymer has a molecular weight from about 500,000 to about 5,000,000 g/mol;

(e) a foam stabilizing, linear or branched $C_{5-12}$ diol with the structure

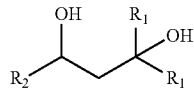

wherein $R_1$=H, $CH_3$, $CH_2CH_3$, $CH_2CH_2CH_3$, $C(CH_3)_3$, $CH(CH_3)_2$ or combinations thereof and $R_2$ is a branched or linear $C_1$-$C_9$ alkyl chain;

(f) from about 0.1 wt. % to about 6.0 wt. % of an aminocarboxylate chelating agent, wherein the chelating agent is ethylenediaminetetraacetic acid (EDTA);

(g) water, wherein said dermal concentrate is substantially free of anionic surfactants, triclosan, and $C_{1-4}$ alcohols for a sufficient time to provide substantial bacterial, microbial, fungal or viral reduction.

2. The method of claim 1 wherein the sufficient contact time is approximately about 1 to about 60 seconds.

3. The method of claim 1 wherein the dermal concentrate is rinsed off the dermal tissue after contact or remains on the dermal tissue after contact.

4. The method of claim 1 wherein the dermal concentrate is diluted with water forming a use solution with a concentrate to water ratio from about 1:1 to about 1:10.

5. A method of reducing bacterial, microbial, fungal or viral population on a dermal tissue of a mammal under hard water conditions comprising the step of:

contacting the dermal tissue of a mammal for a sufficient time to provide substantial bacterial, microbial, fungal or viral reduction with an antimicrobial use solution, wherein the use solution is prepared by diluting a dermal concentrate with water at a concentrate to water ratio of 1:3 to 1:8, wherein the dermal concentrate comprises:

(a) a cationic active ingredient, wherein the cationic active ingredient is an inorganic salt of an aromatic quaternary ammonium containing compound;

(b) from about 0.1% to about 4.5% of a quaternized sugar-derived surfactant;

(c) a foam boosting amine oxide surfactant;

(d) from about 0.05 wt. % to about 18 wt. % of a foam boosting copolymer, wherein the foam boosting copolymer is a dimethyldiallylammonium chloride-acrylamide copolymer, wherein said dimethyldiallylammonium chloride-acrylamide copolymer has a molecular weight from about 500,000 to about 5,000,000 g/mol;

(e) a foam stabilizing, linear or branched $C_{5-12}$ diol with the structure

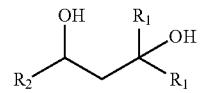

wherein $R_1$=H, $CH_3$, $CH_2CH_3$, $CH_2CH_2CH_3$, $C(CH_3)_3$, $CH(CH_3)_2$ or combinations thereof and $R_2$ is a branched or linear $C_1$-$C_9$ alkyl chain;

(f) from about 0.1 wt. % to about 6.0 wt. % of an aminocarboxylate chelating agent, wherein the chelating agent is ethylenediaminetetraacetic acid (EDTA); and (g) water, and wherein said use solution is substantially free of anionic surfactants and substantially free of triclosan.

6. The method of claim 5 wherein the sufficient contact time is approximately about 1 to about 60 seconds.

7. The method of claim 5 wherein the antimicrobial use solution is rinsed off the dermal tissue after contact or remains on the dermal tissue after contact.

* * * * *